United States Patent
Komvopoulos et al.

(10) Patent No.: US 7,879,418 B1
(45) Date of Patent: Feb. 1, 2011

(54) METHOD FOR DEPOSITING FLUOROCARBON FILMS ON POLYMER SURFACES

(75) Inventors: Kyriakos Komvopoulos, Orinda, CA (US); Satomi Tajima, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 781 days.

(21) Appl. No.: 11/741,408

(22) Filed: Apr. 27, 2007

(51) Int. Cl.
  B32B 1/08 (2006.01)
  B32B 27/06 (2006.01)
  B32B 33/00 (2006.01)
(52) U.S. Cl. .................... 428/36.9; 428/336; 428/421
(58) Field of Classification Search .................. None
  See application file for complete search history.

(56) References Cited

U.S. PATENT DOCUMENTS

| | | | | |
|---|---|---|---|---|
| 4,632,842 A * | 12/1986 | Karwoski et al. | .......... | 427/2.25 |
| 5,034,265 A * | 7/1991 | Hoffman et al. | .......... | 442/126 |
| 5,246,451 A * | 9/1993 | Trescony et al. | .......... | 427/2.25 |
| 5,627,079 A * | 5/1997 | Gardella et al. | .......... | 436/525 |
| 5,876,753 A * | 3/1999 | Timmons et al. | .......... | 427/488 |

OTHER PUBLICATIONS

Cassie, A.B.D. et al.; "Wettability of Porous Surfaces"; 1944, S. Trans. Faraday Soc., vol. 40, pp. 546-551.

Cunge, G. et al.; "$CF_2$ production and loss mechanisms in fluorocarbon discharges: Fluorine-poor conditions and polymerization"; 1999, J. Appl. Phys., vol. 85, No. 8, pp. 3952-3959.

d'Agostino, R. et al.; "The Effect of Power on the Plasma-Assisted Deposition of Fluorinated Monomers"; 1990, J. Polym. Sci.: Part A: Polym. Chem., vol. 28, pp. 3387-3402.

Garrison, Michael D. et al.; "Glow discharge plasma deposited hexafluoropropylene films: surface chemisty and interfacial materials properties"; 1999, Thin Solid Films, vol. 352, pp. 13-21.

Labelle, Catherine B. et al.; "Surface Morphology of PECVD Fluorocarbon Thin Films from Hexafluoropropylene Oxide, 1,1,2,2-Tetrafluoroethane, and Difluoromethane"; 1999, J. Appl. Polym. Sci., vol. 74, pp. 2439-2447.

Labelle, Catherine B. et al.; "Investigation of fluorocarbon plasms deposition from $c\text{-}C_4F_8$ for use as passivation during deep silicon etching"; 2004, J. Vac. Sci. Technol., vol. 22, No. 6, pp. 2500-2507.

Labelle, Catherine B. et al.; "Plasma deposition of fluorocarbon thin films from $c\text{-}C_4F_8$ using pulsed and continuous rf excitation"; 2005, J. Vac. Sci., vol. 23, No. 1, pp. 190-196.

Li, Xi et al.; "Fluorocarbon-based plasma etching of $SiO_2$: Comparison of $C_4F_6$/Ar and $C_4F_8$/Ar discharges"; 2002, J. Vac. Sci. Technol., vol. 20, No. 6, pp. 2052-2061.

(Continued)

Primary Examiner—Ramsey Zacharia
(74) Attorney, Agent, or Firm—Bozicevic, Field & Francis LLP; Bret E. Field

(57) ABSTRACT

A method for forming a carbon-containing layer on a polymeric substrate is disclosed. The polymeric substrate is modified physically and chemically using an inductively coupled plasma process. The carbon-containing layer can be fluorocarbon film with different physicochemical properties and structure.

18 Claims, 17 Drawing Sheets

OTHER PUBLICATIONS

Martin, Ina T. et al.; "Ion effects on $CF_2$ surface interactions during $C_3F_8$ and $C_4F_8$ plasma processing of Si"; 2004, *J. Vac. Sci. Technol.*, vol. 22, No. 5, pp. 2168-2176.

Martin, Ina T. et al.; "Comparison of pulsed and downstream deposition of fluorocarbon materials from $C_3F_8$ and $c$-$C_4F_8$ plasmas"; 2004, *J. Vac. Sci. Technol.*, vol. 22, No. 2, pp. 227-235.

Miyata, Koji et al.; "Kinetics of Radicals in $CF_4$ and $C_4F_8$ Electron Cyclotron Resonance Plasmas"; 1997, *Japan J. Appl. Phys.*, vol. 36, pp. 5340-5345.

Sandrin L. et al.; "Fluorine incorporation in plasma-polymerized octofluorocyclobutane, hexafluoropropylene and trifluoroethylene"; 2001, *Polymer*, vol. 42, pp. 3761-3769.

Sasaki K. et al.; "Correlation between $CF_2$ and $C_xF_y$ densities in $C_4F_8$ plasmas"; 2000, *Thin Solid Films*, vol. 374, pp. 249-255..

Stoffels, W.W. et al.; "Polymerization of fluorocarbons in reactive ion etching plasmas"; 1998, *J. Vac. Sci. Technol.*, vol. 16, No. 1, pp. 87-95.

Tajima, S. et al.; "Effect of reactive species on surface crosslinking of plasma-treated polymers investigated by surface force microscopy"; 2006, *Applied Physics Letters*, vol. 89, pp. 124102-1 thru 124102-3.

Tajima, S. et al.; "Effect of ion energy fluence on the topography and wettability of low-density polyethylene exposed to inductively coupled argon plasma"; 2006, *J. Phys. D*, vol. 39, pp. 1084-1094.

Yasuda, H. et al.; "Critical Evaluation of Conditions of Plasma Polymerization"; 1978, *Journal of Polymer Science*, vol. 16, pp. 743-759.

Yasuda, H. et al.; "Plasma Polymerization Investigated by the Substrate Temperature Dependence"; 1985, *Journal of Polymer Science*, vol. 23, pp. 87-106.

Zheng, Ling et al.; "Studies of film deposition in fluorocarbon plasmas employing a small gap structure"; 2005, *J. Vac. Sci. Technol.*, vol. 23, pp. 634-642.

Tajima et al., "Surface Modification of Low-Density Polyethylene by Inductively Coupled Argon," *J. Phys. Chem. B* 2005, 109, 17623-17629.

\* cited by examiner

US 7,879,418 B1

METHOD FOR DEPOSITING FLUOROCARBON FILMS ON POLYMER SURFACES

STATEMENT AS TO RIGHTS TO INVENTIONS MADE UNDER FEDERALLY SPONSORED RESEARCH OR DEVELOPMENT

This invention was made with Government support under Grant (Contract) Nos. CMS-0528506 and CMS-0127754 awarded by the National Science Foundation. The Government has certain rights to this invention.

CROSS-REFERENCES TO RELATED APPLICATIONS

NOT APPLICABLE

BACKGROUND OF THE INVENTION

Fluorocarbon (FC) film deposition by different plasma techniques has been used in numerous electrical, mechanical, and biomedical applications mainly due to the desirable physicochemical properties (e.g., dielectric constant, surface energy, friction, and wettability) and hemocompatibility of FC films.

It would be desirable to improve the bonding between a fluorocarbon film and the substrate upon which it is formed. For example, in an article including a fluorocarbon film and a substrate, any separation between the fluorocarbon film and the substrate upon which it is disposed can result in problems, especially if the article is a medical device which resides in a patients' body.

Embodiments of the invention address the above problems, and other problems, individually and collectively.

BRIEF SUMMARY

One embodiment of the invention is directed to a method including exposing a polymeric substrate to an inductively coupled plasma, thereby creating a modified surface on the polymeric substrate. A fluorocarbon film is then deposited on the modified surface of the polymeric substrate. At least a portion of the fluorocarbon film is grafted to the polymeric substrate.

Another embodiment of the invention is directed to an article comprising a polymeric substrate comprising a modified surface. A fluorocarbon film is on the modified surface of the polymeric substrate. At least a portion of the fluorocarbon film is grafted to the polymeric substrate.

Embodiments of the invention can be used as polymeric implants and biodevices interacting with soft tissue. They can be used in biological applications requiring durable, hydrophobic, and lubricious surface coatings in particular. Embodiments of the invention relate to fluorocarbon films with desirable in vivo characteristics. The films can have strong interfacial layers that provide for enhanced adhesive strength and can have flexible surface layers for increased lubricity.

These and other embodiments of the invention are described in further detail below.

DETAILED DESCRIPTION

Figures 1A, 1B:
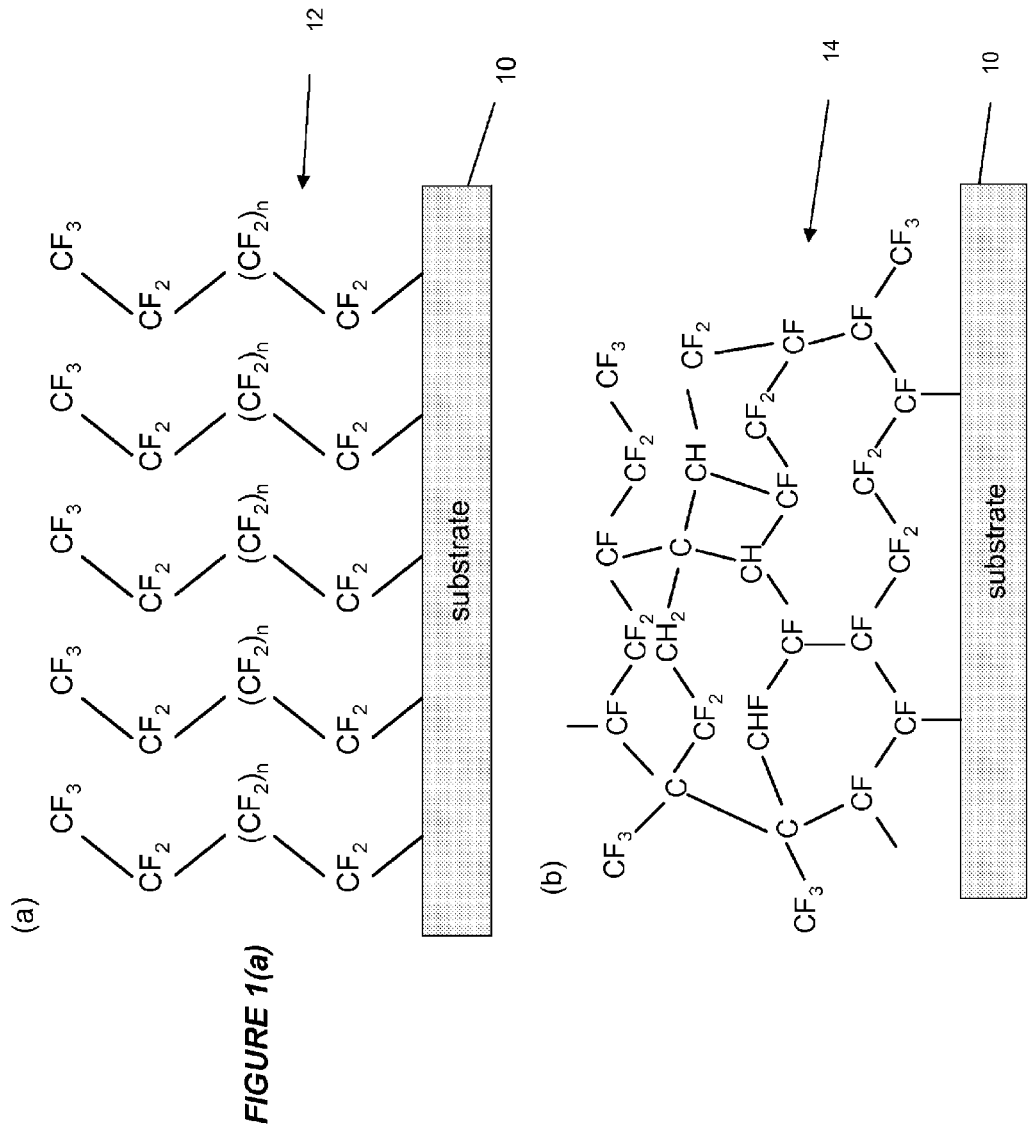
FIGS. 1(a) and 1(b) show chemical structures of typical fluorocarbon films that can be grown under conditions of (a) low-intensity plasma and (b) high-intensity plasma.

Embodiments of the invention are directed to methods for forming articles including polymeric substrates with fluorocarbon films on them. One embodiment of the invention is directed to a method. The method comprises exposing a polymeric substrate to an inductively coupled plasma, thereby creating a modified surface on the polymeric substrate. After the polymeric substrate is exposed to the inductively coupled plasma, a fluorocarbon film is deposited on the modified surface of the polymeric substrate. The inductively coupled plasma can break bonds at the surface of the polymeric substrate so that at least a portion of the fluorocarbon film is grafted (or covalently bonded) to the modified polymeric substrate. If desired, a subsequent layer such as biologically compatible layer may be formed on the fluorocarbon film.

Any suitable polymeric substrate may be used in embodiments of the invention. The substrate may be a layer on a larger surface, or may be a stand-alone substrate that may be in any suitable form. For example, the substrate may be in the form of a plate, a tube, sphere, or complex shape. In preferred embodiments, the substrate is in the form of a tube so that the formed article can be used as an artificial artery, catheter, or the like. The substrate may also have a convex shape, a concave shape, a solid of revolution shape, or any other suitable shape.

The polymeric material in the polymeric substrate may comprise any suitable polymers including homopolymers, copolymers, blends, etc. Examples of suitable polymeric materials include polyethylene, medium-density polyethylene, low-density polyethylene, polymethylmethacrylate, silicones, and polyurethanes. Low-density polymers such as low-density polyethylene are preferred. In some embodiments, high molecular weight polymers such as those that can be used in orthopedic implants or medical devices can be present in the substrate.

Once obtained, the polymeric substrate may be pretreated in any suitable manner. In some embodiments, the polymeric substrate may be exposed to an inductively coupled plasma to modify the surface of the polymeric substrate. An inductively coupled plasma is a plasma that is driven by a current oscillating in a coil, either around or adjacent to the vacuum vessel. The oscillating current gives rise to a time-varying magnetic field in the gas, which induces a local electric field, which accelerates electrons and excites the plasma.

The inductively coupled plasma may have any suitable properties and may comprise any suitable precursor gas. Suitable precursor gases may include oxygen, hydrogen, nitrogen, and noble gases. Different gases may modify the surface of the polymeric substrate in different ways. For example, an oxygen plasma can be used to produce various functional groups on LDPE surfaces and other types of surfaces. In another example, exposure to an inert plasma (e.g., Ar and He) can be used to produce polar functionalities on polymer surfaces. The modification of the surface of the polymeric substrate could also be mechanical in nature. For example, the modified surface of the polymeric substrate can be rougher than an untreated polymeric substrate.

The inductively coupled plasma process may have any suitable process parameters. For example, in some cases, the plasma chamber may be kept between about 50 and about 800 mTorr (e.g., 500 mTorr), the plasma power may be between about 75 and about 1200 Watts (e.g., 1200 W) and the treatment time may be between about 1 minute and about 30 minutes (e.g., about 15 minutes).

After exposing the polymeric substrate to an inductively coupled plasma, a fluorocarbon film may be formed on the polymeric substrate with the modified surface. The fluorocarbon film may be formed using any suitable process including a plasma process. Exemplary plasma processes include capacitively coupled and inductively coupled plasma processes.

Generally, plasma treatments of a polymeric substrate can be achieved by placing the workpiece in contact with the gas to be used in the treatment and imposing high-energy radiation, sufficient to ionize the gas to a plasma state. While not intending to be bound by any particular theory or mechanism of operation, it is believed that the plasma activates the polymer chains that are in contact with the plasma by dissociating covalent bonds in the polymer chains to form free radicals that are reactive with each other or with free radicals in the plasma gas itself. The reactions that then occur at these activated sites will vary with the type of gaseous substance used to form the plasma, or with operating conditions such as the power density, exposure time, working pressure, gas flow rate, temperature, electrode spacing, chamber dimensions, substrate bias voltage, or combinations of these conditions.

Figure 13:
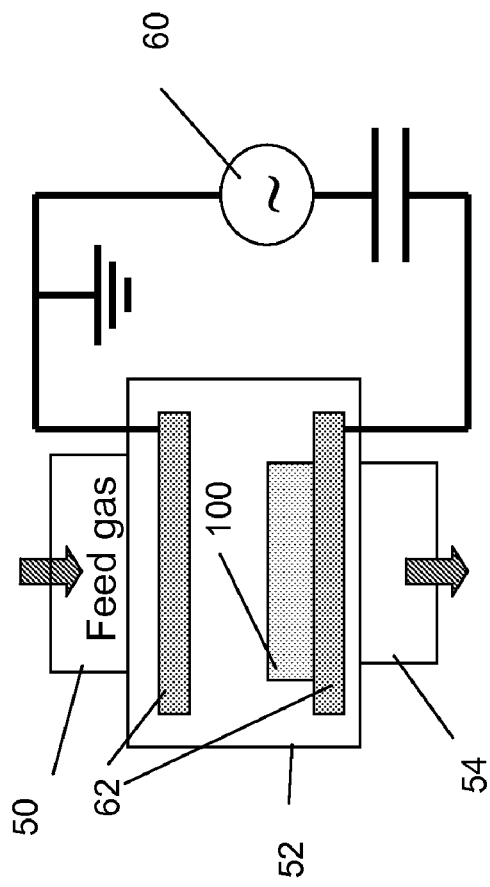
FIG. 13 shows a schematic illustration of a capacitively coupled plasma apparatus.

In a capacitively coupled plasma (CCP) process, electrodes are placed inside a plasma processing chamber, and they ionize precursor gases to form a plasma. An example of a capacitively coupled plasma processing apparatus is shown in FIG. 13. FIG. 13 shows a chamber 52 with an inlet port 50 and a downstream outlet port 54. Electrodes 62 are within the chamber, and are operatively coupled to an rf power source 60. A sample 100 (e.g., the previously described substrate) may rest on one of the electrodes 62. As a feed gas is introduced into the chamber 52, the gas is ionized by the electrodes 62. The ionized gas and neutral atoms or molecules may thereafter interact with the sample 100.

An inductively coupled plasma (ICP) may also be used to deposit the fluorocarbon film on the polymeric substrate. Inductively coupled plasma processes are described above in the pretreatment process. Similar processing conditions can be used in the deposition of the fluorocarbon film; however, the feed gas will be different in the fluorocarbon layer formation process than in the pretreatment process. Examples of suitable feed gases are provided below.

Figure 14:
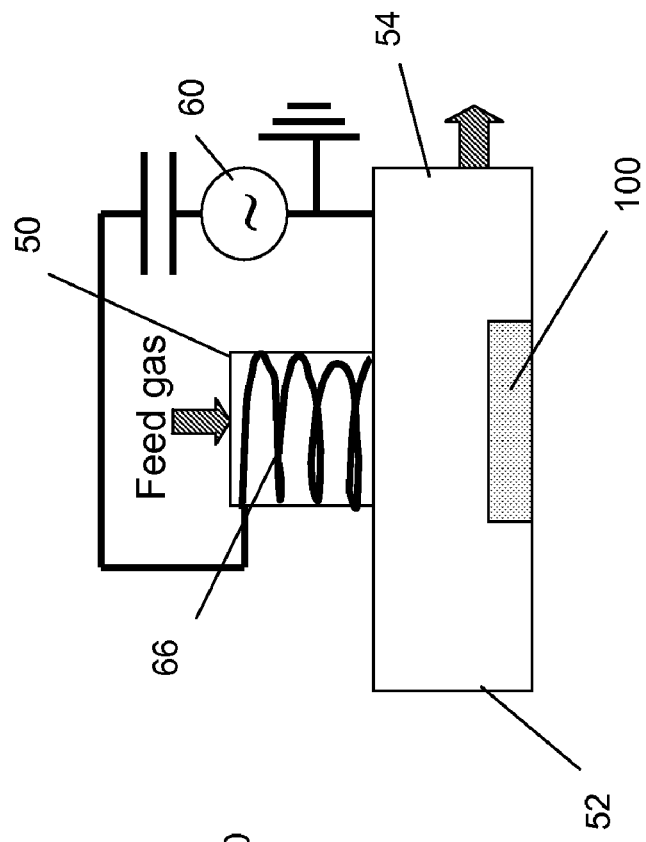
FIG. 14 shows a schematic illustration of an inductively coupled plasma apparatus.

FIG. 14 shows a schematic view of an inductively coupled plasma processing apparatus. It includes a chamber 52 and a sample 100 in the chamber 52. The chamber includes an inlet 50 and an outlet 54. A coil 66 is proximate to the inlet 66 and is electrically coupled to an rf power source 60. The feed gas 50 is introduced into the chamber 52 via the inlet 50, and when it is introduced, it is ionized by the coil 66 and the ionized gases pass into the chamber 52 and interact with sample 100.

In some embodiments, a shield may be used to shield the polymeric substrate from the plasma to control the plasma process and to selectively modify the surface (either physically and/or chemically) of the polymeric substrate. The advantage of using a shielded plasma over pulsed or downstream plasma is that the treatment conditions can be varied without changing the power supply or chamber configuration. The shield may comprise inorganic materials such as Al, Pyrex®, LiF, $CaF_2$, $Al_2O_3$, and $SiO_2$. By using a shield, one can control the types of plasma species and/or radiation reaching the polymeric substrate. For example, Al and other radiation blocking metals may only allow uncharged particles to reach the polymer substrate. On the other hand, LiF, $CaF_2$, $Al_2O_3$, and $SiO_2$ may allow only uncharged particles, UV (ultraviolet) and/or VUV (vacuum ultraviolet radiation) to reach the polymer substrate.

The shield may be stationary within the chamber, or is preferably movable (e.g., coupled to a movable motor) in the chamber so that it can cover or not cover some or all of the polymeric substrate during the surface modification process step. It may also cover or not cover all or some the polymeric substrate during the deposition of the fluorocarbon film. Additionally, the shield can cover the substrate during one process, but not a subsequent process, or vice-versa.

Schematic illustrations of various processing chambers with shields are shown in FIGS. 15(a)-15(d). The shields shown in FIGS. 15(a)-15(d) and other types of shields can be used in the apparatuses shown in FIGS. 13 and 14. Shields can be used in both inductively or capacitively coupled plasma processes, or not at all.

Figure 15B:
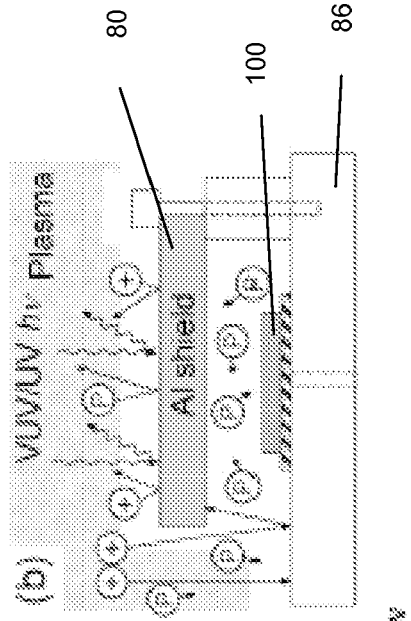
FIGS. 15(a)-15(d) shows schematic illustrations of inductively coupled plasma chambers with shields.
Figure 15A:
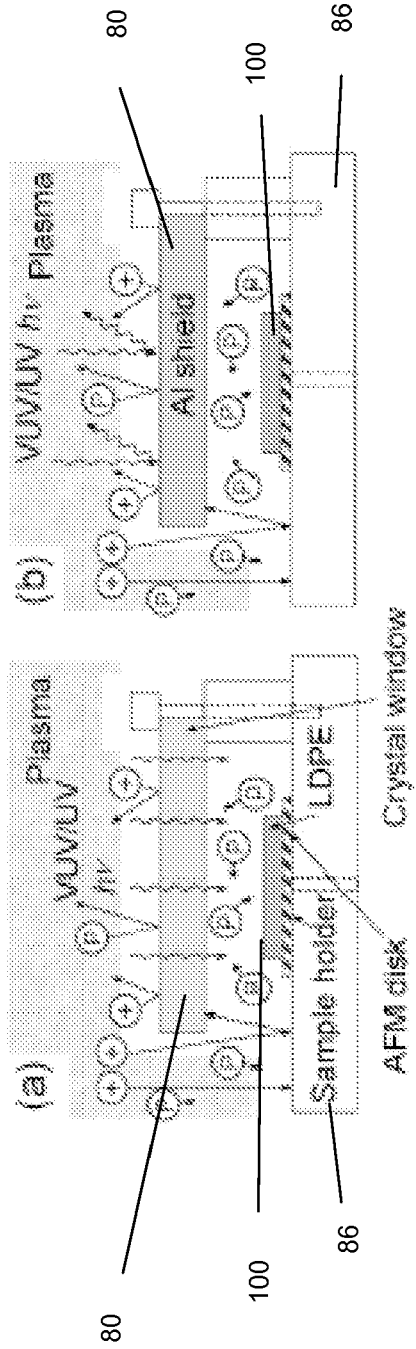

FIG. 15(a) shows a crystal shield apparatus 80 including a crystal shield and a holder that may or may not be able to move the crystal shield. The shield covers a sample 100 on a sample holder 86 and it helps to prevent ionized particles from reaching the sample 100. Neutral particles and UV/VUV radiation can reach the sample 100 through a space that is between the sample holder 86 and the shield (e.g., by a side passage via diffusion).

FIG. 15(b) shows an aluminum shield apparatus 80 including an aluminum shield and a holder that may or may not be able to move the aluminum shield. The shield covers a sample 100 on a sample holder 86 and it helps to prevent ionized particles and VUV/UV radiation from reaching the sample 100. Neutral particles can reach the sample 100 through a space that is between the sample holder 86 and the shield (e.g., by a side passage via diffusion).

Figure 15D:
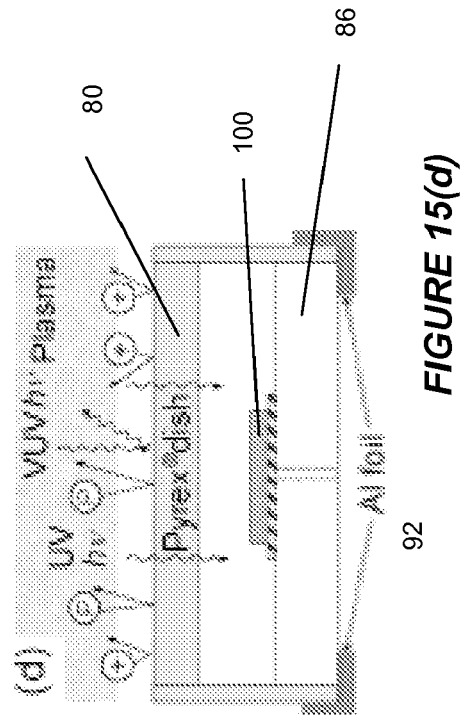
Figure 15C:
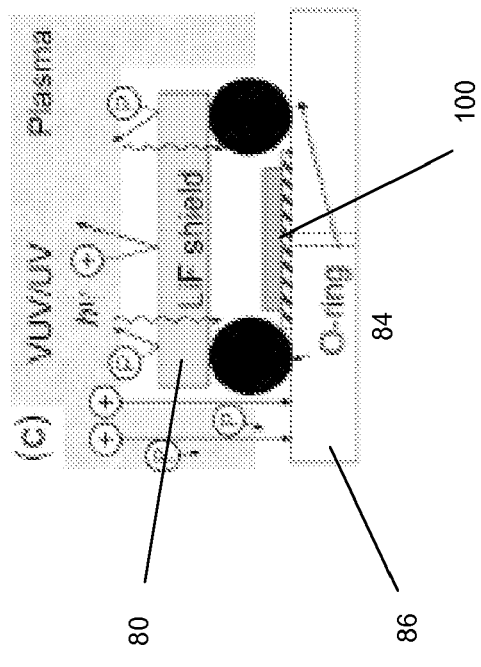

FIG. 15(c) shows a LiF shield apparatus 80 including a LiF shield, and a holder in the form of an o-ring 84. The shield covers a sample 100 on a sample holder 86 and it helps to prevent ionized and neutral particles from reaching the sample 100. UV/VUV radiation can reach the sample 100.

FIG. 15(d) shows crystal shield apparatus 80 including a Pyrex® shield and a holder. The shield covers a sample 100 on a sample holder 86 and it helps to prevent ionized and neutral particles, as well as VUV radiation from reaching the sample 100. UV radiation can reach the sample 100.

As illustrated in FIGS. 15(a)-15(d), by using a shield, the properties of the sample 100 can be selectively altered without modifying processing conditions such as power, gas flow rate, etc. during a plasma process.

The power applied to convert the gas to plasma form can be selected in accordance with the effect sought to be achieved and the desired depth to which the effect will penetrate below the surface into the bulk of the polymer. Penetration depths may be less than one millimeter, or within the range of 1-10 mm or greater in some cases. Penetration depths that are too deep may alter the properties of the underlying substrate in some cases. In some applications, suitable power intensities, expressed in terms of wattage per unit area of the surface to be treated, range from about 2 to about 100 watts per square centimeter.

Other deposition conditions are likewise variable. The exposure time for example can be selected with the considerations similar to those used for the power density. In some cases, exposure times ranging from about 2 minutes to about 60 minutes, and preferably from about 4 minutes to about 30 minutes can be used. Suitable pressures in the plasma chamber can be within the range of about 50 mtorr (6.65 pascals) to about 250 mtorr (33.2 pascals), or from about 80 mtorr (10.6 pascals) to about 230 mtorr (30.6 pascals). The flow rate of the plasma gas across the workpiece surface being treated may vary, typically from about 50 to about 2000 standard cubic centimeters per minute (measured under standard conditions of temperature and pressure, and expressed as sccm), and preferably from about 100 sccm to about 1000 sccm. The deposition process does not require elevated temperatures and can be performed at temperatures less than 50° C., preferably from about 20° C. to about 40° C.

The gas used to deposit the fluorocarbon film may comprise organic fluorides such as trifluoromethane, tetrafluoromethane, tetrafluoroethane, hexafluoroethane, difluoroethylene, and hexafluoropropylene, as well as tetrafluoroethane, hexafluoroethane, and hexafluoropropylene. These or other species can be used individually or as mixtures.

When organic fluorides are used as the treatment gas, it may also be desirable to include in the treatment gas a fluorine scavenger to control the degree of etching on the polymer surface. Examples of fluorine scavengers are hydrogen gas, sulfuric acid gas, methane or mixtures of these gases. Preferred mixtures of gases for use as the treatment gas are $CF_4/H_2$, $CF_4/CH_4$, $C_2H_2F_2/CH_4$, $CHF_3/CH_4$, $C_2H_2F_4/CH_4$, $C_2F_6/CH_4$, and $C_2F_6/CH_4$.

Studies dealing with FC plasmas have shown that film growth can be controlled by $C_xF_y$ ions and neutrals. (Stoffels, W. W. et al., *J. Vac. Sci. Technol. A*, 16:87 (1998); Sasaki, K. et al., *Thin Solid Films*, 374:249 (2000); Cunge, G. and Booth, J. P., *J. Appl. Phys.*, 85:3952 (1999)). For efficient FC film deposition, large monomer precursors (e.g., $C_3F_8$ and $C_4F_8$) are desirable because they produce more $C_xF_y$ ions and neutrals than small monomer precursors (e.g., $CF_4$, $C_2F_4$, and $C_2F_6$). (Stoffels, W. W. et al., *J. Vac. Sci. Technol. A*, 16:87 (1998); Cunge, G. and Booth, J. P., *J. Appl. Phys.*, 85:3952 (1999); Miyata, K. et al., *Jpn. J. Appl. Phys.*, 36:5340 (1997)). Precursor gases, for example, can include $C_xF_y$, where x and y are greater than 2, and the ratio of x to y is about 2 or more than 2. Such fluorocarbons are desirable, since they do not introduce too much fluorine into the plasma process. Too much fluorine can cause unintended etching in some cases.

The FC film properties depend on their chemical composition, which differs from that of the film precursors. FC films with different $CF_3$, $CF_2$, CF, and CCF concentrations can be synthesized, depending on the ion bombardment intensity and vacuum ultraviolet (VUV) and ultraviolet (UV) radiation. In addition, the presence of secondary precursors, such as $H_2$, $O_2$, and Ar, may also affect the chemical composition of FC films. (d'Agostino, R. et al., *J. Polym. Sci.: Part A: Polym. Chem.*, 28:3387 (1990); Li, X. et al., *J. Vac. Sci. Technol. A*, 20:2052 (2002); Zheng, L. et al., *J. Vac. Sci. Technol. A*, 23:634 (2005); Labelle, C. B. et al., *J. Vac. Sci. Technol. A*, 23:190 (2005)). For example, $CF_2$-rich FC films with uncrosslinked microstructures (FIG. 1(a)) can be deposited under low intensities of ion bombardment and VUV/UV radiation (Favia, P. et al., *Plasmas and Polymers*, 1:299 (1996)). The fluorocarbon layer in FIG. 1(a) can be a monolayer in some instances. Films rich in CF and CCF groups exhibiting two-dimensional branching and/or crosslinked microstructures (FIG. 1(b)) can be obtained under plasma conditions of intense ion bombardment and VUV/UV radiation. (d'Agostino, R. et al., *J. Polym. Sci.: Part A: Polym. Chem.*, 28:3387 (1990)).

Figure 12:
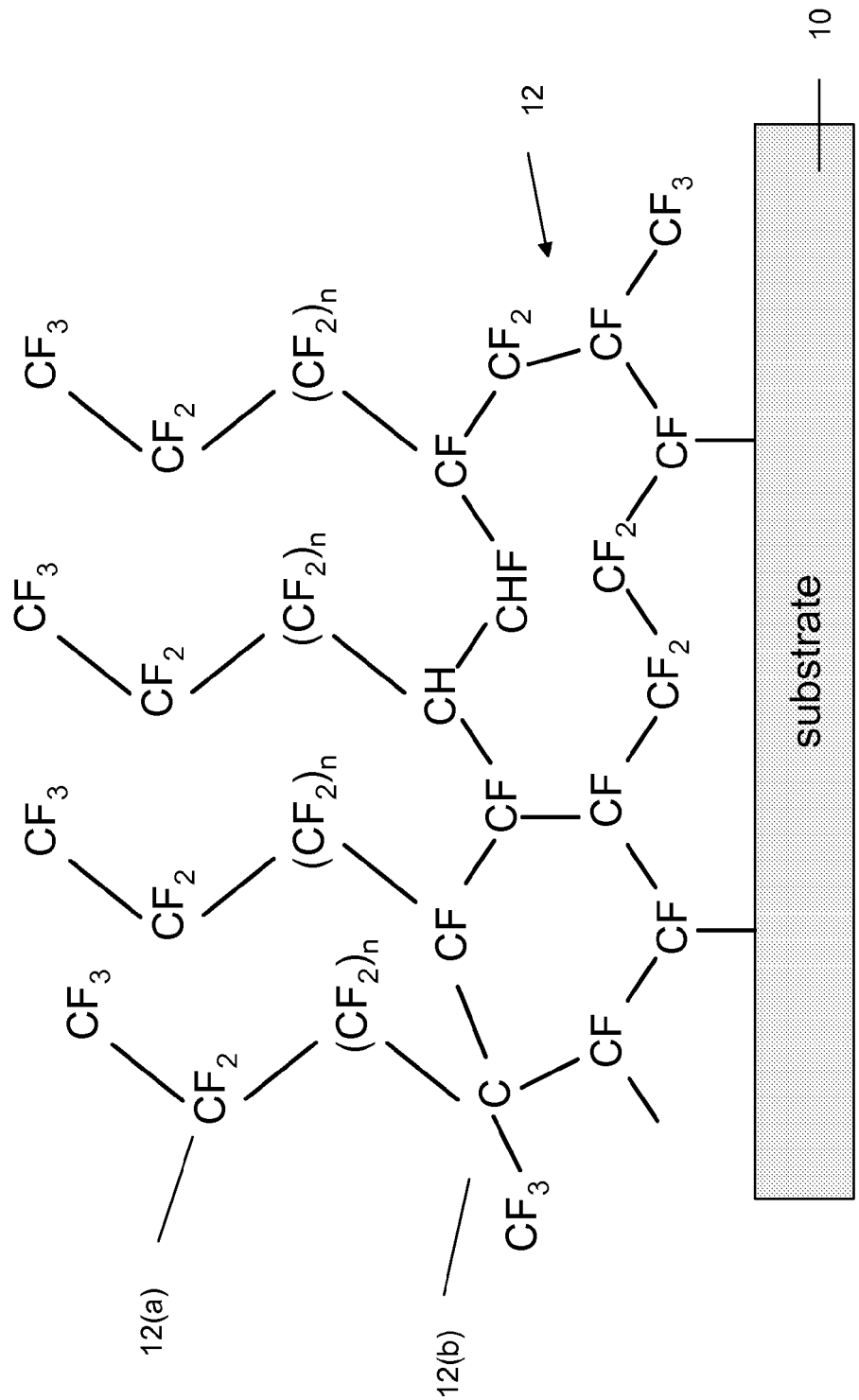
FIG. 12 shows a model of the chemical structure of a hybrid fluorocarbon film grown under shielded plasma conditions.

Also, as shown in FIG. 12, a fluorocarbon film 12 (in this case a hybrid film) on a substrate 10 may include an uncrosslinked region 12(a) and a crosslinked region 12(b). Additional strata of crosslinked and uncrosslinked regions may be present on the substrate in other embodiments of the invention. The crosslinked region 12(b) can provide a solid anchor to the substrate 10, while the uncrosslinked region 12(a) is less rigid and is more flexible and has less friction than the crosslinked region 12(b). This can be desirable as the outer surface of the fluorocarbon film is less likely to scar surrounding tissue. Also, the uncrosslinked region 12(b) can also provide for attachment sites (e.g., $CF_3$ groups) for proteins and the like. It is more difficult to attach proteins to crosslinked fluoropolymer regions, than uncrosslinked fluoropolymer regions.

These crosslinked and uncrosslinked layers may be created by varying the processing conditions during the fluorocarbon film deposition process. For example, more intense plasma processing conditions can be used to produce the crosslinked region 12(b) and less intense plasma processing conditions can be used to produce the uncrosslinked region 12(a). In a capacitively coupled plasma processing chamber, for example, the above described shield can be used to modify the properties of the fluorocarbon film 12. For example, to create an environment where the substrate 10 is exposed to less intense plasma processing conditions to create the uncrosslinked region 12(a), the above-described shield may cover the substrate 10. During the same fluorocarbon film deposition process, the shield can then be moved so that it does not cover the substrate 10. This can result in the creation of the cross-linked region 12(b). In some cases, by simply moving the shield, one can achieve desired properties in the fluorocarbon film 12. Other plasma processing parameters such as temperature, feed gas flow rate, power, etc. need not be changed to vary the properties of the fluorocarbon film 12. In other instances, other process parameters (e.g., the power) can be adjusted to form the crosslinked and uncrosslinked regions.

Subsequently deposited layers may also have any suitable characteristics and may be formed using any suitable process. Subsequently deposited layers may include biocompatible layers including proteins, cells, etc. In some embodiments, a subsequently deposited layer may comprise proteins which can attach to $CF_2$ or $CF_3$ terminal groups in the fluorocarbon film. Cells, such as endothelial cells may subsequently attach to those proteins.

Figure 16:
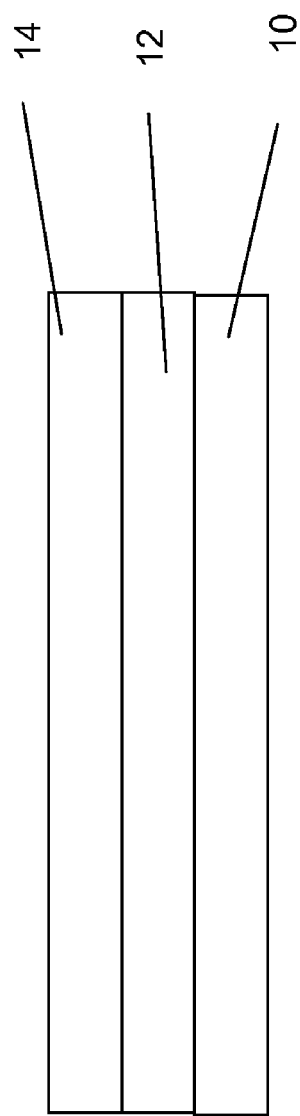
FIG. 16 shows a schematic illustration of an article including three layers.
Figure 17:
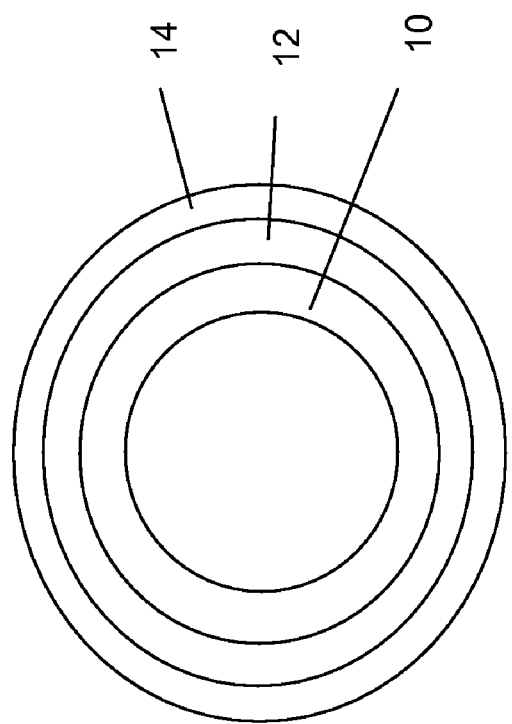
FIG. 17 shows a schematic illustration of a tubular article including three layers.

The articles according to embodiments of the invention may be in any suitable form. Examples of articles to be formed may include artificial arteries, implants, catheters, etc. Schematic cross-sections of suitable articles may include flat composites as shown in FIG. 16, or tubular composites as shown in FIG. 17. The articles in FIGS. 16 and 17 may have a polymeric substrate 10, a fluorocarbon film 12, and a biocompatible layer 14 on the fluorocarbon film 12. The characteristics of each of these layers are described in further detail above and below.

The various layers 10, 12, 14 in the above described articles may have any suitable thickness. For example, the thicknesses of each of the components may be greater than about 10 nanometers in some cases, or greater than about 1 micrometer in other cases.

EXAMPLES

Smooth FC films were synthesized on surface-crosslinked, low-density polyethylene (LDPE) using a capacitively coupled octafluorocyclobutane ($C_4F_8$) plasma treatment. Differences in the nanoscale and microscale film growth mechanisms on LDPE samples with or without a plasma shield were investigated with a wide range of plasma power. Results for the film thickness, wettability, and surface chemistry are interpreted in terms of corresponding plasma conditions to elucidate the effects of plasma species, such as ions, VUV/UV radiation, and uncharged particles, on the growth, morphology, and physicochemical properties of the FC films.

Experimental Procedures

Polyethylene Specimens. Specimens of 1-cm diameter and thickness in the range of 800-900 μm were fabricated by press casting pellets of LDPE (Sigma-Aldrich, St. Louis, Mo.) onto atomic force microscope (AFM) metal disks. X-ray diffraction and differential scanning calorimetry demonstrated that the crystallinity of the LDPE specimens was equal to ~50%. To induce surface crosslinking, the specimens were exposed to plasma generated from a radio frequency (rf) inductively coupled plasma source (Litmas Inc., Charlotte, N.C.). The plasma was produced from a high-purity (99.999%) Ar gas (Praxair, Danbury, Conn.) introduced into the vacuum chamber at a flow rate of 100 sccm under a pressure of 500 mTorr. All the specimens were treated for 15 min under plasma conditions of 1200 W rf power and sample-to-plasma source distance equal to 15 cm, producing an ion energy fluence of $1.8 \times 10^5$ $J/m^2$. More details for the experimental setup and the modification of the physicochemical properties of LDPE under different Ar plasma conditions can be found elsewhere. (Tajima, S. and Komvopoulos, K., *J. Phys. Chem. B*, 109: 17623 (2005); Tajima, S. and Komvopoulos, K., *J. Phys. D: Appl. Phys.*, 39:1084 (2006); Tajima, S. and Komvopoulos, K., *Appl. Phys. Lett.*, 89:124102 (2006)).

Fluorocarbon Film Deposition. FC films were grown on surface-crosslinked LDPE specimens in an rf capacitively coupled plasma reactor (RTE73 AMNS-500-E, Plasmatherm Inc., Kresson, N.J.) with a 29.4-cm plate diameter and plate-to-plate distance equal to 5 cm. The specimens were placed on the grounded (bottom) electrode, which was water-cooled to maintain a substrate temperature of 16-17° C. The reaction gas ($C_4F_8$) was introduced into the chamber at a flow rate of 50 sccm 2 min before initiating film deposition to establish a stable base pressure of 85 mTorr. Film deposition was then performed under conditions of rf power in the range of 50-450 W and working pressure between 85 and 122 mTorr (depending on the power). In all the experiments the deposition time was fixed at 2 min, except one experiment where it was 30 min. The specimens were kept under a pressure of 85 mTorr for 1 min after the film deposition to allow active plasma species to gradually reach equilibrium before turning off the power. The plasma conditions of all the FC film depositions examined in this study are given in Table 1.

TABLE 1

Density of uncharged particles in the plasma, energy/monomer mass, and film thickness (shielded plasma conditions) measured by angle-resolved XPS versus plasma conditions.

| plasma conditions[a] | | density of uncharged particles $n_g$ (x $10^{17}$) | energy/ monomer mass W/FM (MJ/kg) | film thickness[b] t (nm) |
|---|---|---|---|---|
| power W (W) | pressure P (mTorr) | | | |
| 50 | 85 | 1.0 | 7.4 | Ø |
| 100 | 84 | 1.0 | 14.7 | Ø |
| 150 | 86 | 1.0 | 22.1 | 0.26 |
| 200 | 86 | 1.0 | 29.4 | 1.1 |
| 250 | 95 | 1.1 | 36.8 | 1.3 |
| 275 | 96 | 1.1 | 40.4 | 1.6 |
| 300 | 95 | 1.1 | 44.1 | 2.1 |
| 450 | 120 | 1.5 | 66.2 | 2.5 |

[a]deposition time = 2 min
[b]shielded plasma conditions (Ø = incomplete film coverage)

In a series of plasma treatments, the specimens were shielded from the plasma by a 2.54×2.54 cm Al plate, which was placed 2 mm above the specimen surface to prevent ion bombardment and VUV/UV radiation during film growth. The distance from the specimen center to the shield edge was 7.4 mm. Hereafter, the plasma environment obtained with and without the Al shield will be referred to as shielded and unshielded plasma, respectively. The survival rate of $CF_x^+$ (x=1, 2, or 3) ions of incident energy in the range of 30-150 eV after surface impingement is less than 6%. (Martin, I. T. and Fisher, E. R., *J. Vac. Sci. Technol. A*, 22:2168 (2004); Martin, I. T. et al., *J. Vac. Sci. Technol. A*, 22:227 (2004)). Hence, most ions were either absorbed or scattered as uncharged particles after impinging onto the surface of the Al shield. Therefore, only uncharged particles interacted with the crosslinked polymer surface during film growth under shielded plasma conditions.

Microanalysis Techniques. The FC film thickness, surface roughness, and changes in the wettability and chemical characteristics of Ar-treated (crosslinked) LDPE due to FC film deposition were examined with an AFM, ellipsometer, spectroscopic reflectometer (SR), X-ray photoelectron spectroscope (XPS), and goniometer. All the film characterization studies were performed within 0.5-3 h from the film deposition to avoid any aging effects on the measurements.

Film Thickness. The thickness of the FC films grown under unshielded plasma conditions was measured with an ellipsometer (AutoEL™ II, Model A9822, Rudolph Technologies, Inc., Flanders, N.J.) with a wavelength of 633 nm and a SR (210 XP Scanning UV Nanospec/DUV Microspectrophotometer, Nanometrics Inc., Milpitas, Calif.). The films were deposited on 10-cm-diameter p-type Si(100) wafers approximately 5 min after treating the wafers with 49% HF for 10 min to remove the native oxide layer. Average and standard deviation values of each film thickness were obtained from ten measurements. Differences in the film thickness estimated with the previous techniques were on the order of the experimental scatter (standard deviation).

The FC film thickness t and refractive index were calculated from the measured ellipsometry parameters using customized software (double-layer absorbing film (DAFIBM)). The refractive index of the FC films synthesized under different plasma conditions was found to be in the range of 1.38-1.43, consistent with previous results. (Labelle, C. B. et al., *J. Vac. Sci. Technol. A*, 22:2500 (2004)). Film thickness measurements were obtained with an accuracy of ±3 Å, assuming a film refractive index of 1.4. The same refractive index value was used to estimate the film thickness from the SR measurements.

In view of the very thin FC films grown under shielded plasma conditions, the film thickness was determined from angle-resolved XPS or ellipsometry measurements. XPS spectra were acquired with a Perkin-Elmer PHI 5400 ESCA system (without charge neutralization or monochromator) using Al—Kα (1486.6 eV) X-ray source and a 54.7° angle relative to the analyzer axis. The sampling depth h is given by $$h = 3\lambda \sin\theta, \quad (1)$$

where $\lambda$ is the inelastic mean free path ($\lambda$=2.5 nm for FC films) 12 and $\theta$ is the take-off angle measured from the surface normal. XPS spectra were acquired from different depths (0-7.5 nm) by varying $\theta$ between 0° and 90°. Survey spectra were collected in the binding energy range of 0-270 eV with 187 eV pass energy and 0.5 eV resolution. The film thickness was determined from the depth at which the peaks corresponding to the Si substrate (Si2s and Si2p$_3$) disappeared from the XPS spectrum.

Film Surface Morphology. The morphology of the FC films at various length scales was studied with an AFM (NanoScope IV, Veeco Metrology, Santa Barbara, Calif.) operated in the contact mode. AFM scans of 1×1 and 10×10 μm² surface areas were obtained with a resolution of 256×256 pixels, i.e., pixel-to-pixel distance (sampling length) equal to 3.9 and 39.2 nm, respectively. The sampling length indicates the scale at which the roughness parameters were determined from the AFM images. Thus, it may be presumed that the 1 μm² and 100 μm² area scans are indicative of the nanoscale and microscale surface topographies of the FC films. Statistical surface topography parameters, such as centerline average roughness $R_a$, root-mean-square roughness $R_q$, skewness, and kurtosis, calculated from 1 μm² and 100 μm² AFM surface scans were used to quantify the changes in the film surface topographies. For statistical analysis, surface roughness parameters were calculated as averages of six measurements obtained from two to three specimens of the same FC film.

Film Surface Chemical Analysis. To examine the variation of the FC film wettability with the plasma power, static contact angle measurements were performed at room temperature using a drop shape analysis system (DSA10, Krtiss GmbH, Hamburg, Germany). Average contact angles were calculated from four contact angle measurements obtained from four specimens of the same FC film (i.e., 16 contact angle measurements for each film).

Film chemical compositions were determined from XPS spectra of 1-mm-diameter sampling surface area and 5.3 nm depth using an electron take-off angle $\theta$=45°. Survey spectra were collected with pass energy of 187 eV and resolution of 1.0 eV to identify the elements present on the surfaces. For chemical bond identification, detail scans of core level C1s, O1s, and F1s were collected with pass energy of 35.75 eV and resolution of 0.05 eV. To compensate for surface charging effects, all binding energies in the C1s core level spectra were referenced to the $\underline{C}F_2$ peak centered at 291.5 eV or the $\underline{C}$—H/$\underline{C}$—C peak centered at 285.0 eV. After Shirley background noise subtraction, polar functionalities were determined by curve fitting the C1s spectra with 70% Gaussian-30% Lorenzian (GL) distributions of full width at half maximum equal to 2.0 eV (AugerScan 3, RBD Enterprises, Inc., Bend, Oreg.). A goodness-of-fit parameter (corresponding to the error-mean-square parameter) of less than 3 was used in the curve fitting algorithm. Table 2 shows the peak positions of the C—F bonds used to curve fit the C1s spectra. (Clark, D. T. in *Photon, Electron and Ion Probes of Polymer Structure and Properties*, Eds. Dwight, D. W.; Fabish, T. J.; Thomas, H. R., American Chemical Society, Washington, D.C., 1981, pp. 247-291; Horie, M., *J. Vac. Sci. Technol. A*, 13:2490 (1995); Fuoco, E. R. and Hanley, L., *J. Appl. Phys.*, 92:37 (2002)).

TABLE 2

Binding energy of functional groups identified by Gaussian-Lorentzian curve fitting of the C1s core level XPS spectra.

| group designation | functional groups | binding energy (eV) |
|---|---|---|
| —$\underline{C}F_3$ | —$\underline{C}F_3$, $\underline{C}F_3$—CF | 293.5 |
| —$\underline{C}F_2$— | —$\underline{C}F_2$, —$\underline{C}F_2$—CF—, —$\underline{C}F_2$—$\underline{C}F_2$— | 291.5 |
| —$\underline{C}F$—$CF_n$ | —$\underline{C}F$—$CF_2$, —$\underline{C}F$—CF—CF—, $CF_3$—$\underline{C}$—$CF_3$ | 289.9 |
| —$\underline{C}F$— | —$\underline{C}F$— | 288.7 |
| —$\underline{C}$—$CF_n$— | —$\underline{C}$—$CF_2$, —$\underline{C}$—$CF_3$, —CF—$\underline{C}$—CF—, —CF—$\underline{C}$—$CF_2$— | 286.9 |
| —$\underline{C}$—C— | —$\underline{C}$—C—, —$\underline{C}$—H— | 285.0 |

The FC films synthesized by capacitively coupled $C_4F_8$ plasma are hybrids of the two chemical structures shown in FIGS. 1(a) and 1(b). The concentration of each structure in the FC film was determined from the degree of crosslinking, evaluated in terms of the F/C ratio, percent of crosslinking, and connectivity number. The F/C ratio was calculated from the curve-fitted C1s spectra using the relationship (Winder, E. J. and Gleason, K. K., *J. Appl. Polym. Sci.*, 78:842 (2000)):

$$F/C = \frac{(3 \times \% \underline{C}F_3) + (2 \times \% \underline{C}F_2) + (1 \times \% \underline{C}F - CF_n) + (1 \times \% \underline{C}F)}{100}, \quad (2)$$

where n=1, 2, or 3. The weighting factor (1, 2, or 3) of each term in Eq. (2) denotes the number of F atoms attached to each underlined C atom. The higher the F/C ratio, the more F atoms attached to C atoms and, hence, the lower the degree of crosslinking.

The degree of crosslinking is proportional to the sum of the areas under the $\underline{C}F$—$CF_n$, $\underline{C}F$, $\underline{C}$—$CF_n$, and $\underline{C}$—$C/\underline{C}$—H peaks divided by the total area under the C1s peak. This is because only these chemical bonds contribute to chain crosslinking. Thus, the percent of crosslinking X can be expressed as (Garrison, M. D. et al., *Thin Solid Films*, 352:13 (1999))

$$X = \frac{(\%\,\underline{C}F - CF_n + \%\,\underline{C}F + \%\,\underline{C} - CF_n + \%\,\underline{C} - C)}{100}. \quad (3)$$

Since the average connectivity number m represents the average number of network-forming bonds per atom, it can be used to evaluate the rigidity of an amorphous material. (He, H. and Thorpe, M. F., *Phys. Rev. Lett.*, 54:2107 (1985); Döher, G. H. et al., *J. Non-Crystal. Solids*, 42:87 (1980)). Thus, the FC film rigidity was examined by considering the number of bonds available to other carbon atoms, (Winder, E. J. and Gleason, K. K., *J. Appl. Polym. Sci.*, 78:842 (2000)) using the relationship $$m = \frac{(\%\,\underline{C}F_3) + (2 \times \%\,\underline{C}F_2) + (3 \times \%\,\underline{C}F - CF_n) +}{100} \quad (4)$$
$$\phantom{m =}\frac{(3 \times \%\,\underline{C}F) + (4 \times \%\,\underline{C} - CF_n) + (4 \times \%\,\underline{C} - C)}{100},$$

where the weighting factor (1, 2, 3, or 4) of each term in Eq. (4) indicates the number of available bonds in each underlined C atom. For rigid atomic bonds characterized by a high degree of crosslinking m>2.4, while for flexible atomic bonds associated with a low degree of crosslinking m<2.4. (Winder, E. J. and Gleason, K. K., *J. Appl. Polym. Sci.*, 78:842 (2000); He, H. and Thorpe, M. F., *Phys. Rev. Lett.*, 54:2107 (1985)). The previously discussed methods (Eqs. (2)-(4)) were used to determine the F concentration and the degree of crosslinking in each FC film by calculating the areas under the GL distributions fitted to the C1s spectra.

Results and Discussion

Plasma Conditions. Due to the ion density dependence of $C_4F_8$ dissociation, variations in the plasma power resulted in pressure changes (Table 1). The density of uncharged particles (i.e., neutrals, radicals, metastables, and atoms) in the plasma $n_g$, determined from the ideal gas law.

$$n_g = PV/kT \quad (5)$$

where P is the pressure, V ($=3.65 \times 10^{-3}$ m$^3$) is the chamber volume, k ($=1.381 \times 10^{-23}$ J/K) is the Boltzmann constant, and T($\approx$290 K) is the temperature of the grounded electrode, and the values of the W/FM factor calculated for F=$3.4 \times 10^{-5}$ mol/s (=50 sccm) and M=0.2 kg/mol are given in Table 1.

For W/FM less than a threshold value (energy deficient region), more energy is needed to form the film than the monomer and the film thickness increases with the plasma power, (Yasuda, H. and Wang, C. R., *J. Polym. Sci.: Polym. Chem. Ed.*, 23:87 (1985); Sandrin, L. et al., *Polymer*, 42:3761 (2001)) while above the W/FM threshold (monomer deficient region), excessive fragmentation of the monomer molecules leads to the formation of highly reactive species (e.g., $CF_3^+$, $CF_3$, F) which induce film ablation and the film thickness either remains constant (Yasuda, H. and Hirotsu, T., *J. Polym. Sci. Polym. Chem. Ed.*, 16:743 (1978)) or decreases. (Chen, R. et al., *J. Appl. Polym. Sci.*, 56:615 (1995)). High W/FM values represent conditions of intense ion bombardment conducive to film etching. (Silverstein, M. S. et al., *Polym. Eng. Sci.*, 36:2542 (1996); Coburn, J. W. and Winters, H. F., *J. Vac. Sci. Technol.*, 16:391 (1979)). The threshold W/FM depends on the bonding energy of the precursor monomer and the reactor configuration (Yasuda, H. and Wang, C. R., *J. Polym. Sci.: Polym. Chem. Ed.*, 23:87 (1985)) and can be empirically determined from film thickness and roughness measurements.

Figure 2:
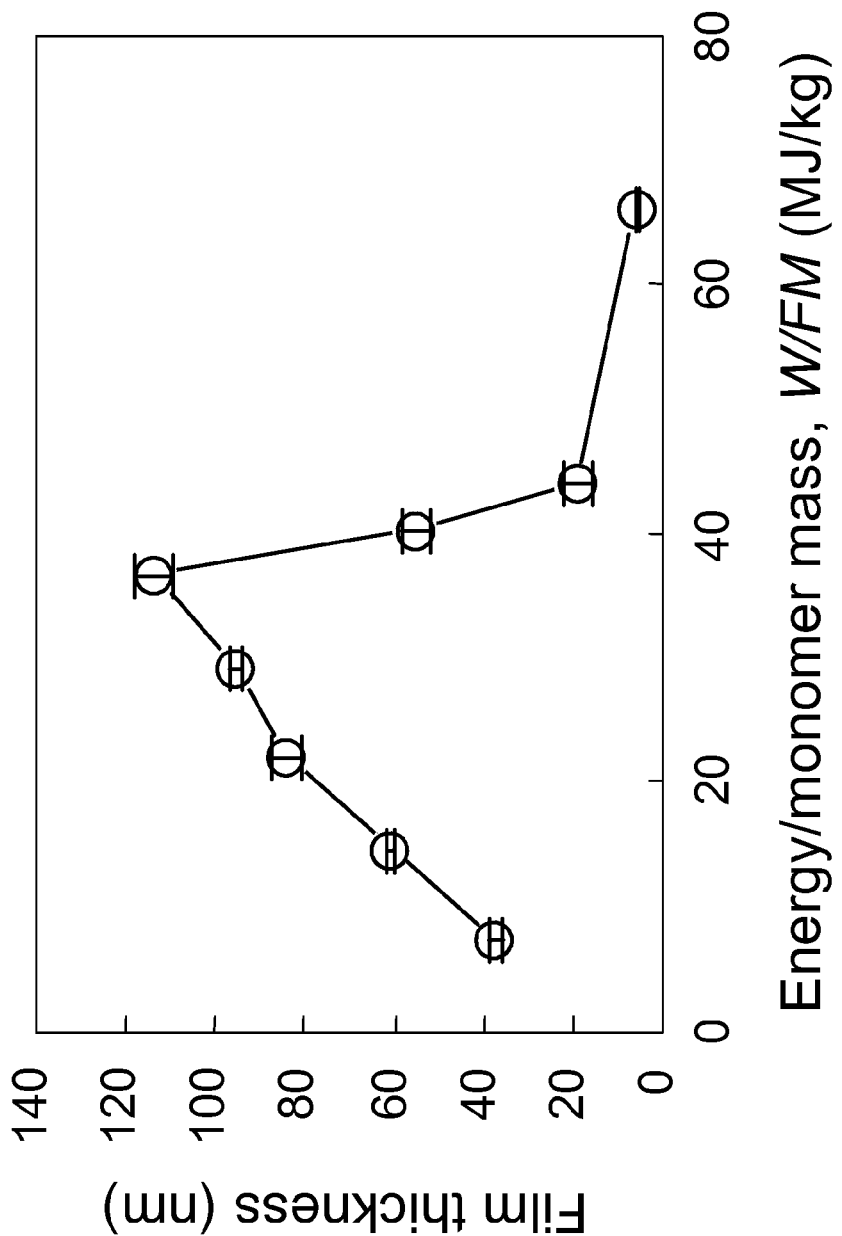
FIG. 2 shows a graph illustrating fluorocarbon film thickness versus energy/monomer mass (unshielded plasma conditions).

Film Growth. The thickness of the FC films grown on Si under unshielded plasma conditions versus energy/monomer mass is shown in FIG. 2. The film thickness increases with W/FM up to ~37 MJ/kg and then decreases sharply in the range of 37-41 MJ/kg, much faster than what was observed in a previous study. (Sandrin, L. et al., *Polymer*, 42:3761 (2001)). This pronounced decrease in film thickness is possibly due to the increased dissociation of F, $CF_3^+$, CF, and/or $CF_3$ species which cause film ablation. (Sandrin, L. et al., *Polymer*, 42:3761 (2001)). In view of the results shown in FIG. 2, the transition from energy-deficient region to monomer-deficient region (W/FM threshold) for deposition time equal to 2 min is predicted to be in the range of 36-41 MJ/kg.

The thickness of the FC films synthesized under shielded plasma conditions (determined from angle-resolved XPS) is given in Table 1. The appearance of the Si2s and Si2p$_3$ peaks in the XPS spectra corresponding to the smallest sampling depth for W/FM<15 MJ/kg indicated that these FC films were discontinuous. A steady increase in film thickness was found for W/FM>15 MJ/kg. Thus, a transition from energy-deficient region to monomer-deficient region was not observed in the absence of ion bombardment and VUV/UV radiation.

Figure 3:
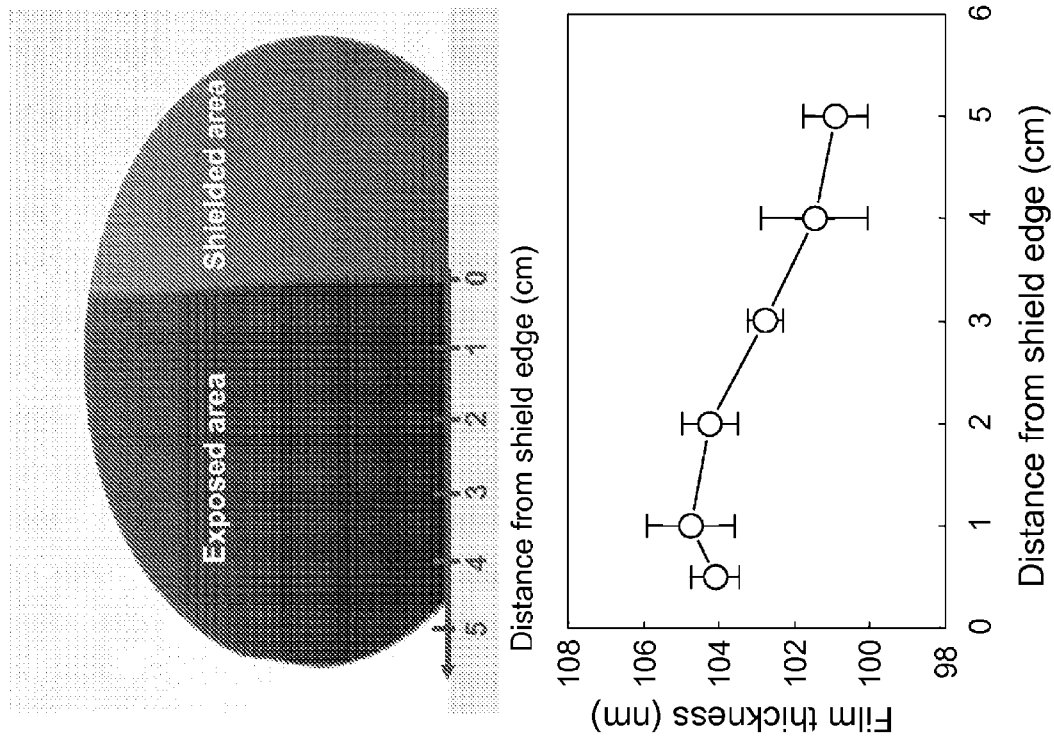
FIG. 3 shows fluorocarbon film thickness versus distance from shield edge (unshielded plasma conditions). The locations of the exposed area where the film thickness was measured are shown in the photograph above the film thickness plot.

Differences in the concentration of uncharged particles below the edge and the center of the shield promoted surface diffusion of the uncharged particles. It has been argued that diffusion of uncharged particles is the dominant film deposition process under shielded plasma conditions. (Zheng, L. et al., *J. Vac. Sci. Technol. A*, 23:634 (2005)). According to Eq. (5), the density of the uncharged particles in the plasma is independent of plasma power. (Although increasing the power from 50 to 450 W resulted in a pressure increase from 85 to 120 mTorr, the effect of this pressure change on the density of the uncharged particles was very small, as shown in Table 1.) However, the thickness of the FC films deposited under shielded plasma conditions increased with the plasma power. This suggests that the former diffusion model, (Zheng, L. et al., *J. Vac. Sci. Technol. A*, 23:634 (2005)) which accounts only for uncharged particles from the plasma, cannot fully describe the film growth mechanism under shielded plasma conditions. Hence, it is desirable to include in the diffusion model the density of the uncharged particles generated from the impingement of energetic ions onto the metal shield. The number of ion-shield collisions depends on the ion density and is proportional to W/FM. Experimental evidence suggests that the $CF_2$ concentration near the plasma-surface interface increases with the ion energy. (Martin, I. T. and Fisher, E. R., *J. Vac. Sci. Technol. A*, 22:2168 (2004)). Thus, uncharged particles produced from ion-shield collisions appear to play an important role in the deposition of thick films under shielded plasma conditions and high W/FM To investigate this hypothesis, a Si wafer was placed on the ground electrode with one-third of its surface covered by another Si wafer during plasma treatment at a power of 150 W. The film thickness (measured with a SR) versus distance from the shield edge is shown in FIG. 3. The higher film thickness near the shield edge is attributed to uncharged particles generated from ion-shield collisions and the smaller film thickness in the exposed area away from the shield-edge to the effects of ions and uncharged particles from the plasma. This finding demonstrates that, in addition to ions and uncharged particles from the plasma, uncharged particles from ion-shield collisions play an major role in the film deposition process.

The film deposition rate under shielded plasma conditions was much less than that under unshielded plasma conditions. The results shown in FIG. 2 indicate that the increase of the deposition rate in the range of W/FM<37 MJ/kg was predominantly due to ions that exhibit a higher adsorption rate than uncharged particles. Above the W/FM threshold, excessive ion bombardment promoted film sputtering, resulting in the decrease of the film thickness. Diffusion of uncharged particles from the plasma and ion-shield collisions controlled film deposition under shielded plasma conditions. In this environment, the film thickness increased continuously with W/FM (Table 1) due to the absence of ion bombardment.

Figure 4:
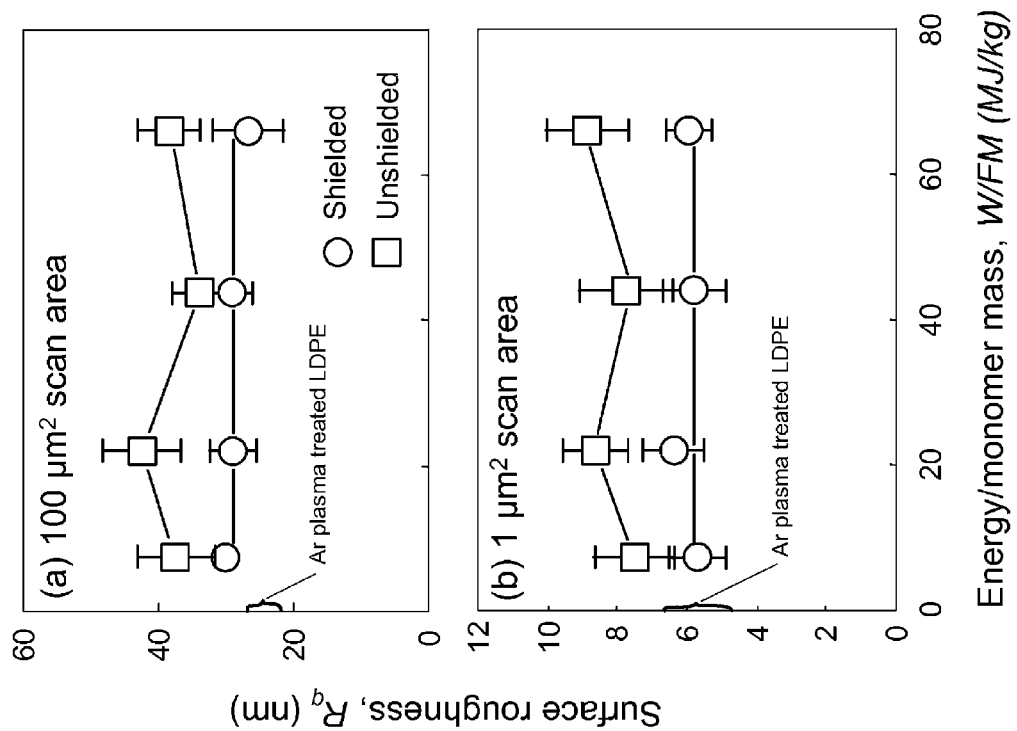
FIG. 4 shows surface roughness of fluorocarbon films grown under (O) shielded and (□) unshielded plasma conditions: (a) 100 $\mu m^2$ and (b) 1 $\mu m^2$ AFM surface images.

Film Surface Morphology. FIG. 4 shows the surface roughness $R_q$ as a function of W/FM for both shielded and unshielded plasma conditions. The roughness range of Ar-treated LDPE is also shown for reference. As mentioned earlier, the roughness data for 100 μm$^2$ and 1 μm$^2$ scan areas can be considered to be representative of the microscale and nanoscale surface topographies. Since the $R_a$ data showed similar trends with those shown in FIG. 4 (although on average they were lower by ~27% than the $R_q$ data) they are not presented here for brevity. Both microscale and nanoscale skewness varied between −0.6 and 0.6, indicating that the asperity heights exhibited Gaussian distributions, while the kurtosis assumed values in the range of 2-5 for both length scales. The film roughness for shielded plasma conditions was close to that of Ar-treated LDPE, especially in the nanoscale roughness measurements. The nanoscale and microscale roughness of the FC films synthesized under unshielded plasma conditions were about 1.2-1.5 times higher than those of the films grown under shielded plasma conditions and that of Ar-treated LDPE over the entire W/FM range. For shielded plasma conditions, both $R_a$ and $R_q$ roughness parameters exhibited small fluctuations in the W/FM range examined in this study. These roughness variations will be explained later by examining the AFM images of the film topographies.

Figure 5:
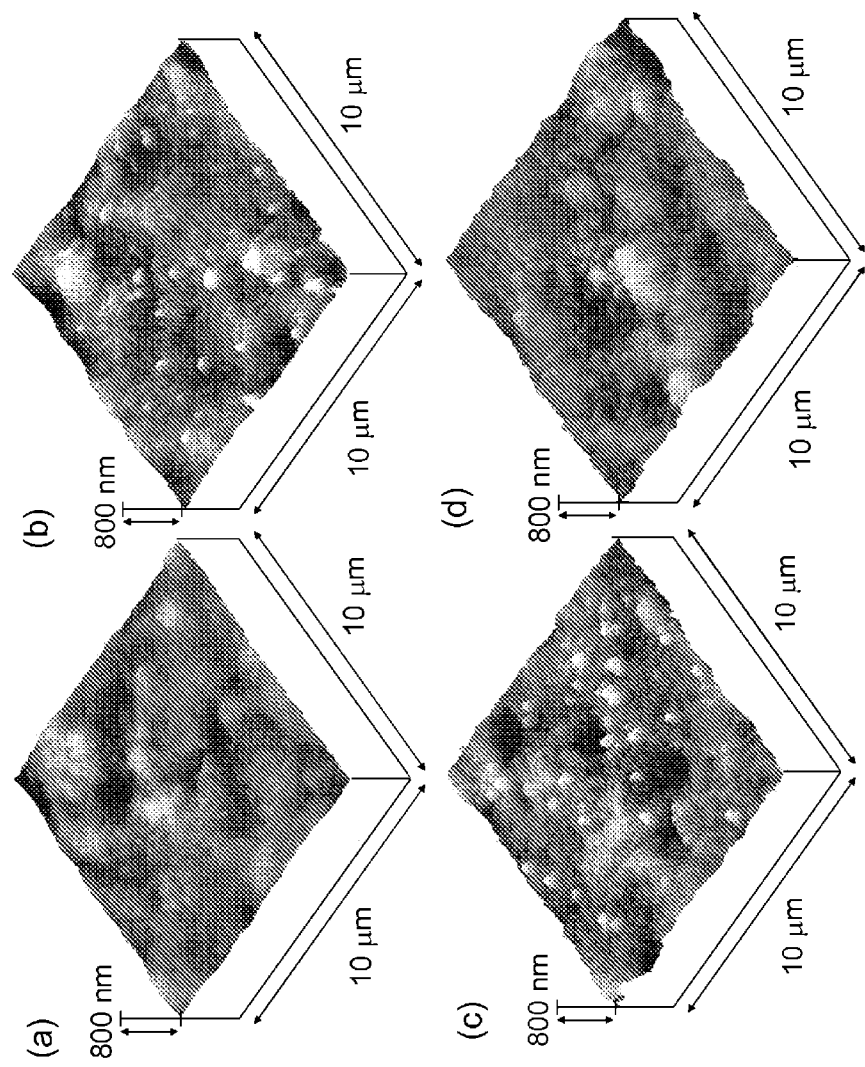
FIG. 5 shows microscale surface topographies of (a) Ar-treated LDPE and fluorocarbon films grown under (b) shielded plasma conditions (W/FM=66.2 MJ/kg) and (c), (d) unshielded plasma conditions (W/FM=22.1 and 66.2 MJ/kg).

Qualitative comparisons of surface topography maps provided further insight into microscale and nanoscale roughness changes. FIG. 5 shows representative microscale topographies of Ar-treated LDPE and FC films grown under shielded and unshielded plasma conditions. Film microtopographies similar to that of Ar-treated LDPE (FIG. 5(a)) were obtained under shielded plasma conditions for W/FM≦44.1 MJ/kg. However, high energy/monomer mass (e.g., W/FM=66.2 MJ/kg) lead to the formation of small asperities and nanoparticles that resulted in slight surface roughening (FIG. 5(b)). Despite these surface changes, AFM imaging indicated that the underlying morphology of the FC films grown under shielded plasma conditions was similar to that of Ar-treated LDPE. The similar microtopographies of Ar-treated LDPE and FC films deposited under shielded plasma conditions for W/FM≦44.1 MJ/kg are consistent with the invariance of microscale roughness under these conditions (FIG. 4(a)). The small changes in $R_q$ for W/FM=66.2 MJ/kg are attributed to the formation of small asperities and nanoparticles on the FC film surfaces.

Microscale morphologies of FC films grown under unshielded plasma conditions for relatively low and high energy/molecular mass are shown in FIGS. 5(c) and 5(d), respectively. A film morphology similar to that shown in FIG. 5(c) was also observed for W/FM=7.4 MJ/kg. Based on particle measurements obtained from three different scans, the average particle size and height corresponding to FIG. 5(c) was found to be 562±111 nm and 145±47 nm, respectively. For unshielded plasma conditions, the particle density increased with W/FM from 7.4 to 22.1 MJ/kg. Particle formation diminished for W/FM>44.1 MJ/kg, while uniform etch pits emerged for W/FM=66.2 MJ/kg due to the intensified ion bombardment (FIG. 5(d)).

Particle formation at high pressures has been attributed to gas phase polymerization. (Sandrin, L. et al., *Polymer*, 42:3761 (2001)). In the present study, more gas phase polymerization was encountered for plasma power equal to 150 W than 50 W under a pressure of ~85 mTorr (Table 1). Thus, gas phase polymerization occurred under conditions conducive to the development of high ion density plasma. Excess ion bombardment promoted etching of the polymerized nanoparticles. The particles produced from gas phase polymerization in this study were much smaller and less dense than those generated from $C_3F_6$ and $C_2F_3H$ plasmas. (Sandrin, L. et al., *Polymer*, 42:3761 (2001)). In addition to particle formation by microscale gas-phase polymerization, unshielded plasma conditions and W/FM<22.1 MJ/kg yielded numerous asperities of average size and height (determined from measurements obtained from three different scans) equal to 181±27 nm and 41±7 nm, respectively. Hence, the formation of particles and asperities under unshielded plasma conditions resulted in higher $R_q$ values than those of Ar-treated LDPE (FIG. 4(a)).

FIGS. 4(a) and 5 indicate that nanoscopic particles, asperities, and etch pits were the main surface features of the film microtopographies; however, the effect of these features on the film roughness was marginal. Asperity formation on the film surfaces was encountered under both shielded (FIG. 5(b)) and unshielded (FIG. 5(c)) plasma conditions. The initial stage of film growth can be described by the Stranski-Krastanov growth model (Ohring, M., *Materials Science of Thin Films, Deposition and Structure*, 2$^{nd}$ ed., Academic Press, San Diego, Calif. (2002)) comprising the initial growth of a layer tightly bonded to the substrate and the subsequent formation of asperity islands on this layer surface. In addition to the development of asperity islands, particle formation due to gas phase polymerization occurred under shielded plasma conditions and high energy/monomer mass (W/FM=66.2 MJ/kg) or unshielded plasma conditions and intermediate to low energy/monomer mass (W/FM≦22.1 MJ/kg).

Figure 6:
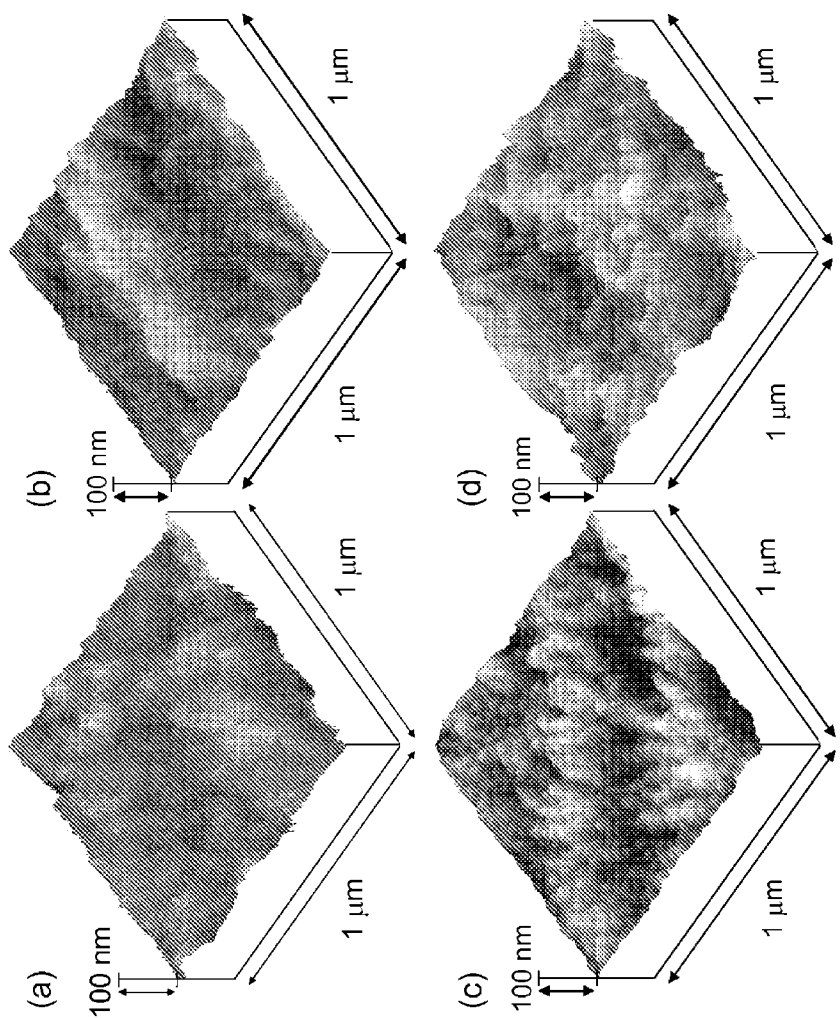
FIG. 6 shows nanoscale surface topographies of (a) Ar-treated LDPE and fluorocarbon films grown under shielded plasma conditions for (b) W/FM=22.1 MJ/kg, (c) W/FM=44.1 MJ/kg, and (d) W/FM=66.2 MJ/kg.
Figure 7:
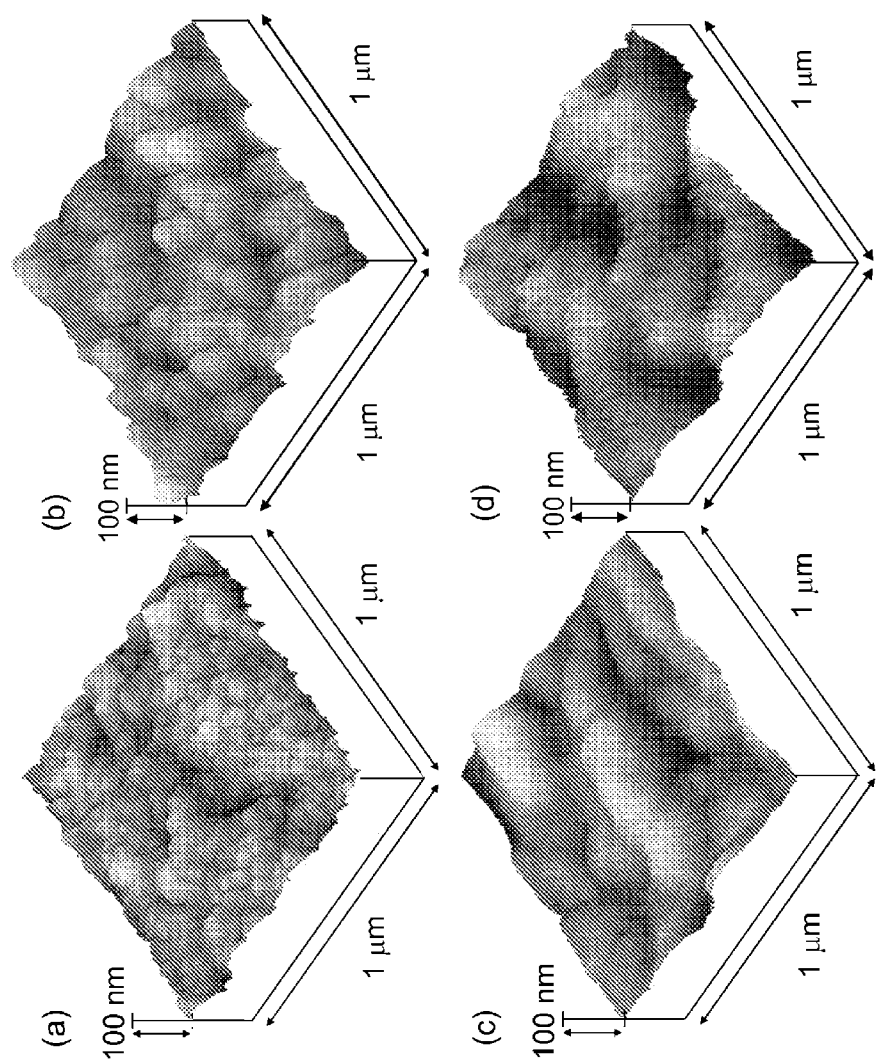
FIG. 7 shows nanoscale surface topographies of fluorocarbon films grown under unshielded plasma conditions for (a) W/FM=7.4 MJ/kg, (b) W/FM=22.1 MJ/kg, (c) W/FM=44.1 MJ/kg, and (d) W/FM=66.2 MJ/kg.

FIGS. 6 and 7 show representative AFM images of the nanoscale topographies of Ar-treated LDPE and FC films grown under shielded and unshielded plasma conditions. The morphology of Ar-treated LDPE comprises numerous nanoscopic asperities (FIG. 6(a)). A comparison of the film surfaces for shielded plasma conditions (FIGS. 6(b)-6(d)) indicates that increasing the energy/monomer mass resulted in asperity coarsening. This is further documented by statistical results of the asperity size and height for shielded plasma conditions given in Table 3.

TABLE 3

Size and height of asperities on the surfaces of fluorocarbon films grown under shielded plasma conditions.

| energy/monomer mass W/FM (MJ/kg) | asperity size (nm) | asperity height (nm) |
|---|---|---|
| ∅ | 37.0 ± 7.1 | 9.4 ± 2.5 |
| 7.4 | 36.2 ± 9.5 | 11.0 ± 3.4 |
| 22.1 | 41.7 ± 9.2 | 8.6 ± 3.0 |

TABLE 3-continued

Size and height of asperities on the surfaces of fluorocarbon films grown under shielded plasma conditions.

| energy/monomer mass W/FM (MJ/kg) | asperity size (nm) | asperity height (nm) |
|---|---|---|
| 44.1 | 59.4 ± 14.6 | 11.2 ± 2.4 |
| 66.2 | 95.8 ± 22.6 | 15.9 ± 5.1 |

∅ = Ar-treated LDPE

The enlargement of the asperities is attributed to the increase of the density of uncharged particles produced from ion-shield collisions with W/FM. The asperity size became less uniform for W/FM=66.2 MJ/kg, probably due to the shadowing effect of the tallest grains, a characteristic feature of the zone 1 growth model. (Thornton, J. A., *Ann. Rev. Mater. Sci.*, 7:239 (1977)). The grains formed under shielded plasma conditions are similar to the zone 1 grains produced from $C_2H_2F_4$ plasma. (Labelle, C. B. and Gleason, K. K., *J. Appl. Polym. Sci.*, 74:2439 (1999))

The nanoscale morphologies of the films grown under unshielded plasma conditions (FIG. 7) illustrate the evolution of grain growth with increasing W/FM Grain growth exhibiting a shadowing effect was not observed under unshielded plasma conditions even for the lowest value of energy/monomer mass (7.4 MJ/kg). Instead, polygon grains of average base length equal to 62±20 nm (calculated from 15 grains of three surface scans) were found on the film surface (FIG. 7(*a*)). The formation of such grains on FC films has not been observed previously. These polygon grains were flat and fairly uniform, i.e., similar to those of the zone 3 growth model. (Thornton, J. A., *Ann. Rev. Mater. Sci.*, 7:239 (1977)). Increasing the energy/monomer mass to 22.1 MJ/kg promoted coalescence of a few polygon grains, resulting in larger grains (FIG. 7(*b*)). The different grain structures produced under shielded and unshielded plasma conditions is associated with the increase of the plasma ion energy. Both ion bombardment intensity and heat at the film surface were higher in the unshielded plasma environment and increased much more with W/FM. For unshielded plasma conditions at W/FM>44.1 MJ/kg, the surface morphology comprised large and smooth protrusions devoid of grain structures (FIG. 7(*c*)). The increase of the ion bombardment intensity with the plasma power (W/FM=66.2 MJ/kg) resulted in microscale and nanoscale etch pits of average peak-to-valley width equal to 10 nm and depth of 2-3 nm (FIG. 7(*d*)).

Figure 8A:
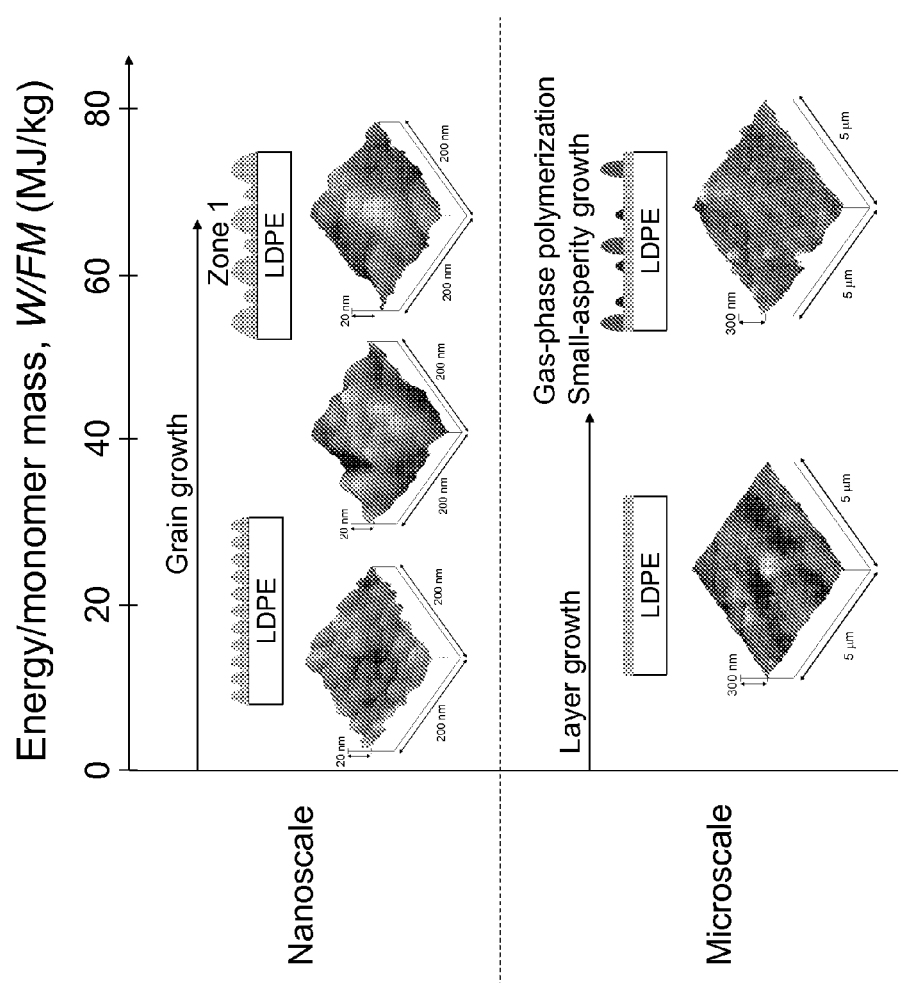
FIGS. 8(a) and 8(b) show fluorocarbon film growth mechanisms under (a) shielded and (b) unshielded plasma conditions for different energy/monomer mass. The x-coordinate of the upper corner of each AFM image indicates the approximate W/FM value of the corresponding surface topography.
Figure 8B:
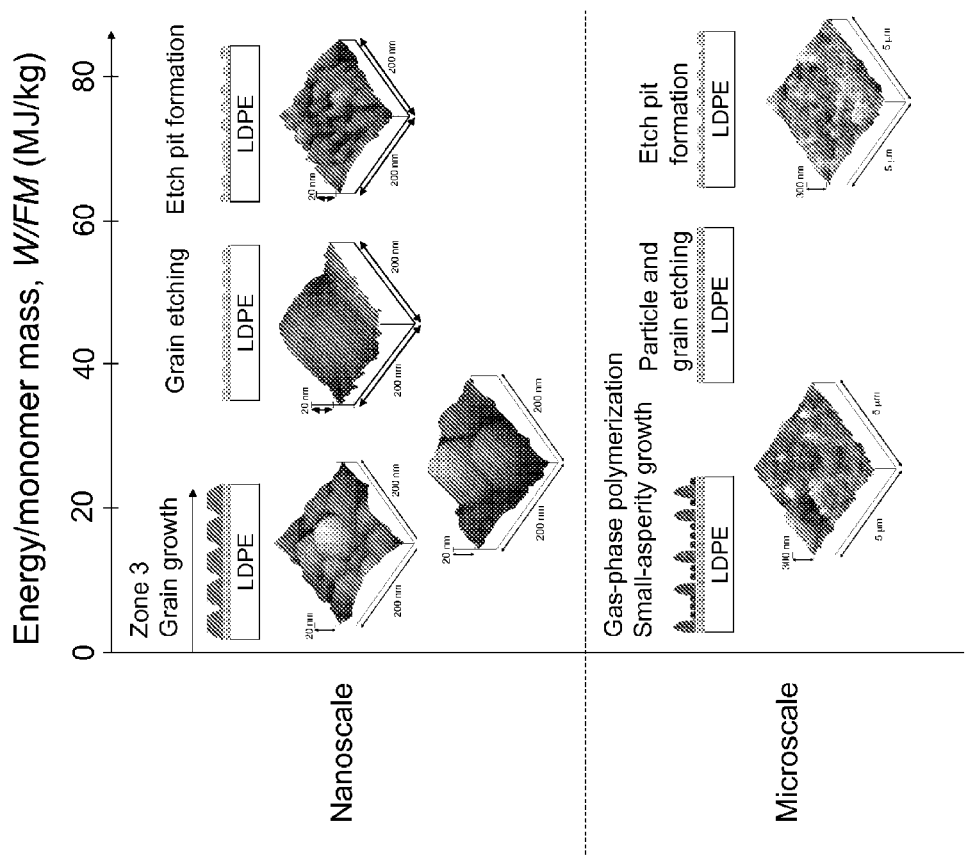

The grain growth mechanisms under shielded and unshielded plasma conditions observed in FIGS. 5-7 are presented in the form of nanoscale and microscale growth maps in FIGS. 8(*a*) and 8(*b*), respectively. These maps demonstrate the significance of different plasma species, such as ions, VUV/UV radiation, and uncharged particles on the FC film morphology in terms of energy/monomer mass and feature scale. For shielded plasma conditions, the film growth characteristics are similar to those of the zone 1 growth model, while for unshielded plasma conditions, film growth resembles that of the zone 3 growth model. (Thornton, J. A., *Ann. Rev. Mater. Sci.*, 7:239 (1977)).

Figure 9:
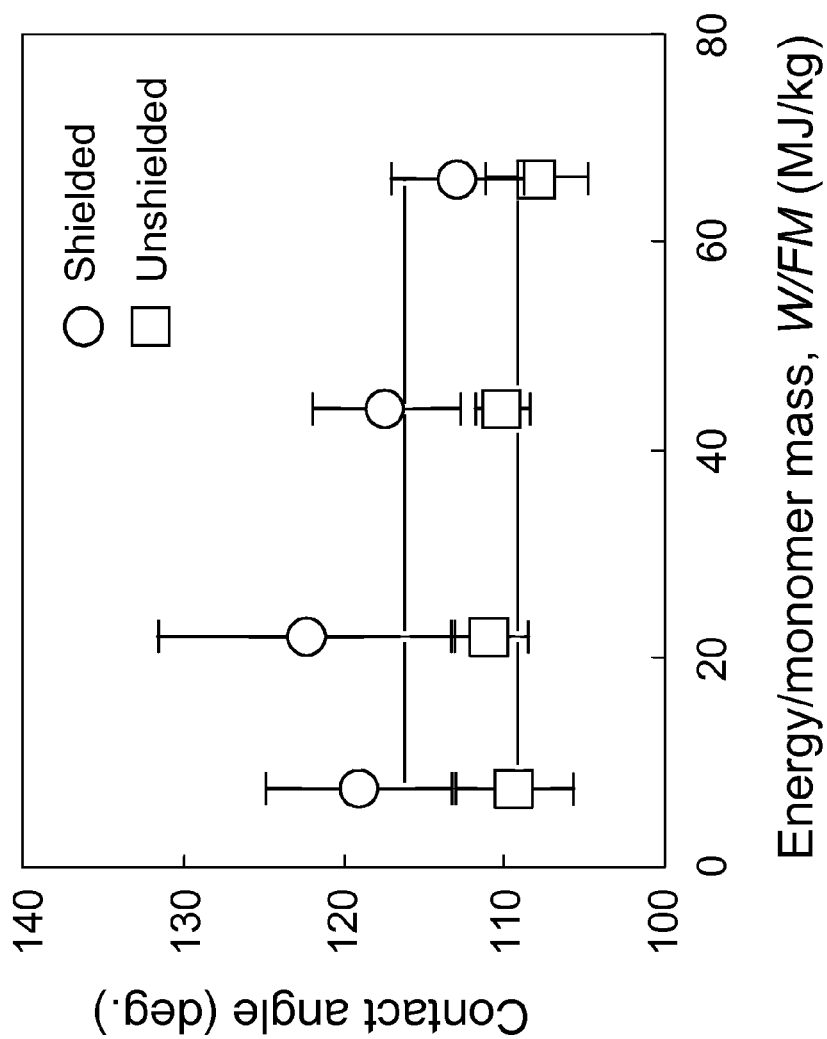
FIG. 9 shows static contact angle of fluorocarbon films grown under (O) shielded and (□) unshielded plasma conditions versus energy/monomer mass.

Film Hydrophobicity. FIG. 9 shows that the static contact angles of the FC films were higher than those of Ar-treated LDPE (33.7±5.9°). The greater scatter in the contact angle data for shielded plasma conditions at relatively low W/FM values is attributed to the incomplete surface coverage by the deposited thin films (Table 1). The high contact angles shown in FIG. 9 are indicative of the hydrophobicity of the FC films. Shielded plasma conditions produced more hydrophobic film surfaces than unshielded plasma conditions, possibly due to $CF_2$ enrichment of the films. The low degree of crosslinking in the absence of ion bombardment and VUV/UV radiation effects (shielded plasma conditions) resulted in $CF_2$-rich films (FIG. 1(*a*)). This postulate is supported by the results of the FC film chemical composition presented in the following section. In view of the statistical error, it may be inferred that the data of FIG. 9 reveal a marginal effect of the energy/monomer mass on the hydrophobic behavior of FC films grown under these plasma conditions.

The contact angle measurements could be affected by the surface roughness. Usually, rough surfaces yield higher contact angles than smooth surfaces of the same chemical composition. The surface roughness effect on the contact angle can be interpreted in terms of the roughness factor, defined as the ratio of the true surface area to the apparent area of the imaged surface. (Wenzel, R. N., *Ind. Eng. Chem.*, 28:988 (1936); Wenzel, R. N., *J. Phys. Colloid. Chem.*, 53:1466 (1949); Johnson, Jr. R. E. and Dettre, R. H. in *Contact Angle, Wettability, and Adhesion*, Ed. R. F. Gould, Adv. Chem. Ser., vol. 43, American Chemical Society, Washington, D.C., 1964, pp. 112-135; Cassie, B. D. and Baxter, S., *Trans. Faraday Soc.*, 40:546 (1944)). The very small roughness factors (<1.6) of both microscale and nanoscale topographies indicated that the formation of particles and asperities (FIG. 5(*c*)), etch pits (FIGS. 5(*d*) and 7(*d*)), and grains (FIGS. 6 and 7) exhibited a secondary effect on the contact angle measurements.

Figure 10A:
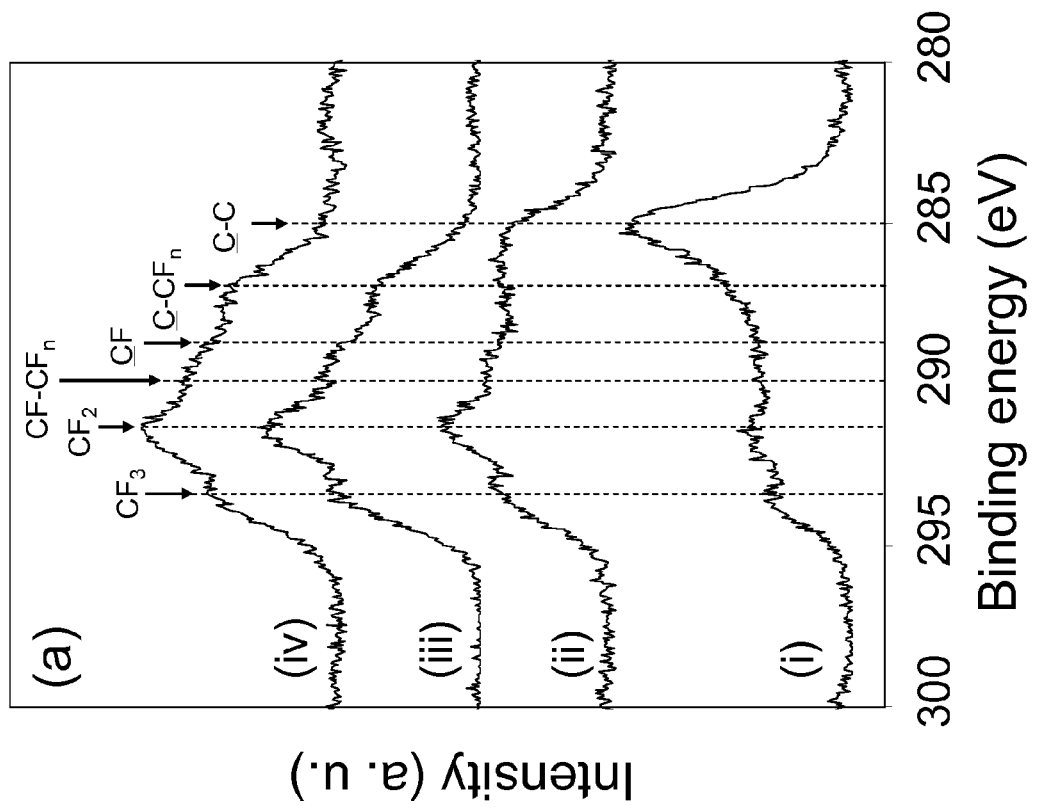
FIGS. 10(a) and 10(b) show C1s core level XPS spectra of fluorocarbon films grown under (a) shielded and (b) unshielded plasma conditions for (i) W/FM=7.4 MJ/kg, (ii) W/FM=22.1 MJ/kg, (iii) W/FM=44.1 MJ/kg, and (iv) W/FM=66.2 MJ/kg.
Figure 10B:
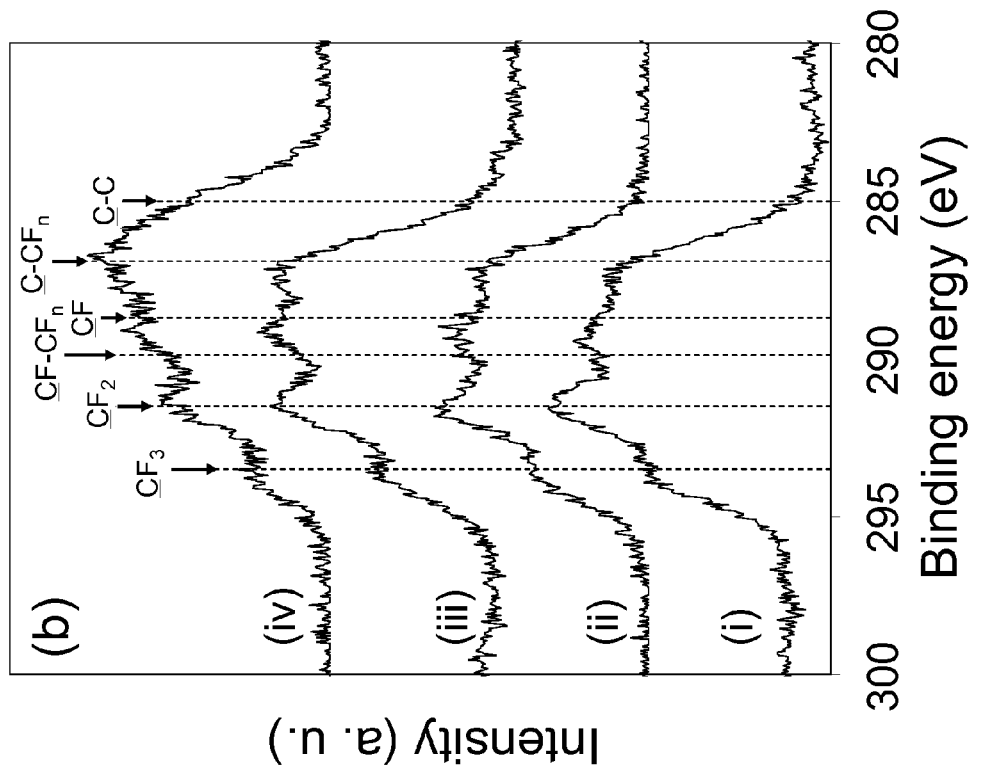

Film Surface Chemistry. FIG. 10 shows the effect of energy/monomer mass on the C1s core level XPS spectra of the FC films. The main feature in the spectra for shielded plasma conditions (FIG. 10(*a*)) is the dominance of the C̲$F_2$ peak for W/FM≧22.1 MJ/kg, suggesting the formation of $CF_2$-rich films with structures similar to that shown in FIG. 1(*a*). The high intensity of the C̲—C peak for W/FM=7.4 and 22.1 MJ/kg is attributed to the LDPE substrate. This peak was present only in the spectra of the thinner films obtained under shielded plasma conditions (Table 1) in which the XPS sampling depth was greater than the film thickness. For W/FM≧44.1 MJ/kg, the C̲—C peak disappeared from the C1s spectrum, confirming the full coverage of the LDPE surface by the thicker FC films grown under those plasma conditions. The similar intensities of the C̲$F_2$, C̲F, and C̲—$CF_n$ peaks in the C1s spectra for unshielded plasma conditions (FIG. 10(*b*)) reveal a high number of C̲F and C̲—$CF_n$ bonds, implying the development of a crosslinked film structure similar to that shown in FIG. 1(*b*). In addition, the intensities of the C̲F and C̲—$CF_n$ peaks increased with W/FM much more than the intensities of the C̲$F_2$ and C̲$F_3$ peaks. This trend illustrates an enhancement of the crosslink density with increasing energy/monomer mass for film deposition under unshielded plasma conditions, consistent with previous results. (Labelle, C. B. et al., *J. Vac. Sci. Technol. A*, 22:2500 (2004))

Figures 11A, 11B:
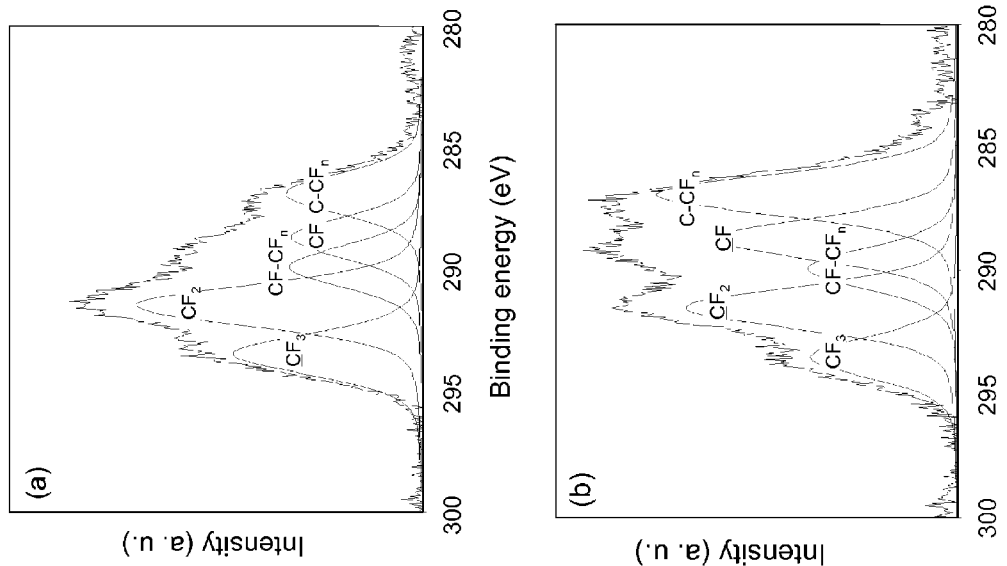
FIG. 11 shows high-resolution C1s core level XPS spectra of fluorocarbon films grown under (a) shielded and (b) unshielded plasma conditions for W/FM=44.1 MJ/kg. (Curve fitting was based on the peak positions given in Table 2.)

FIG. 11 shows high-resolution C1s spectra of FC films deposited under shielded and unshielded plasma conditions for W/FM=44.1 MJ/kg. The spectrum shown in FIG. 11(*a*) is similar to that of a FC film grown by the pulsed plasma method. (Martin, I. T. et al., *J. Vac. Sci. Technol. A*, 22:227 (2004)). The spectra include GL curve fits at the F—C peak positions given in Table 2. Results for the chemical bonds, F/C ratio, crosslinking percentage, and connectivity number are given in Table 4.

TABLE 4

Chemical bonding, F/C ratio, percentage of crosslinking, and connectivity number obtained from high-resolution C1s core level XPS spectra of fluorocarbon films grown under shielded and unshielded plasma conditions.*

| measurement | | shielded plasma conditions | | unshielded plasma conditions |
|---|---|---|---|---|
| | | 2 min | 30 min | 2 min |
| chemical bond (%) (FIG. 11) | —$CF_3$ | 21.6 | 22 | 13.3 |
| | —$CF_2$— | 32.6 | 39 | 24.5 |
| | —$CF$—$CF_n$— | 15.2 | 13.2 | 13.5 |
| | —$CF$— | 15.0 | 14.2 | 21.7 |
| | —$C$—$CF_n$— | 15.5 | 11.6 | 27.1 |
| | —$C$—$C$— | 0 | 0 | 0 |
| F/C (Eq. (2)) | | 1.60 | 1.71 | 1.24 |
| crosslinking X (%) (Eq. (3)) | | 46 | 39 | 62 |
| Connectivity m (Eq. (4)) | | 2.39 | 2.29 | 2.76 |

*Energy/monomer mass = 44.1 MJ/kg; deposition time = 2 or 30 min.

The results presented in FIG. 11 and Table 4 show that the films deposited under unshielded plasma conditions possessed higher concentrations of $\underline{C}F$ and $\underline{C}$—$CF_n$ bonds, whereas shielded plasma conditions produced films with higher $CF_2$ and $CF_3$ contents. In addition, unshielded plasma conditions yielded lower F/C ratio, higher percentage of crosslinking, and higher connectivity number than shielded plasma conditions. These results provide further evidence that unshielded plasma conditions resulted in more crosslinked films (FIG. 1(b)), while shielded plasma conditions favored the deposition of $CF_2$-rich films with less crosslinked structures (FIG. 1(a)). Hence, the higher contact angles for shielded plasma conditions (FIG. 9) can be attributed to the formation of films with higher $CF_2$ concentrations. These findings illustrate the important roles of ion bombardment and VUV/UV radiation in FC film crosslinking and are in agreement with the results of a previous study on the effect of plasma species on polymer crosslinking. (Tajima, S. and Komvopoulos, K., Appl. Phys. Lett., 89:124102 (2006))

Table 4 shows that the film grown in 2 min under shielded plasma conditions exhibited 46% crosslinking, suggesting that the film chemical structure might be a mixture of those shown in FIGS. 1(a) and 1(b). However, the data for 30 min deposition time and same plasma conditions indicate that the F/C ratio increased and the crosslink density and connectivity number decreased with the increase of the deposition time. In view of this finding, it may be inferred that the interfacial chemical structure was a mixture of the chemical structures depicted in FIGS. 1(a) and 1(b), while the chemical structure of the outer layer of the film resembled that shown in FIG. 1(a). The presumed structure of this hybrid film is shown in FIG. 12. Such growth model is plausible because in the absence of ion bombardment and VUV/UV radiation the conditions were conducive to the growth of $CF_2$-rich films, especially for relatively long deposition time. In addition to the higher hydrophobicity of the films grown under shielded plasma conditions, the lower connectivity number might be indicative of the formation of FC chains with increased flexibility. The combination of a crosslinked (strong) interfacial region and a compliant surface layer are beneficial to the bonding strength and surface lubricity of the FC films. These properties are highly desirable for polymer implants and biodevices interacting with soft tissue. Therefore, polymer treatment with uncharged particles alone is especially advantageous for biological applications requiring durable, hydrophobic, and lubricious (low friction) surface coatings.

In this study, FC films with significantly different chemical structures were obtained in the presence of energetic ion bombardment and VUV/UV radiation. The simultaneous effects of these plasma species resulted in the formation of crosslinked FC films, as evidenced by the increase of the $\underline{C}F$ and $\underline{C}$—$CF_n$ peak intensities in the C1s spectrum (FIG. 11(b)) and the lower F/C ratio, higher crosslink percentage, and higher connectivity number (Table 4). Ion bombardment and VUV/UV radiation resulted in the abstraction of F from the FC chains, leading to the formation of radicals that reacted with each other to produce three-dimensional crosslink networks in the film structure. Hence, the C—F bonds in the films grown under unshielded plasma conditions produced a structure similar to that shown in FIG. 1(b), characterized by greatly reduced chain mobility. Since these films are stiffer than those obtained from uncharged particles alone, they are suitable for applications involving high surface shear rates, such as FC films used to lubricate hard disks of magnetic recording drives.

The growth mechanisms of thin FC films synthesized under conditions resulting in surface interaction with uncharged particles only (shielded plasma conditions) or ion bombardment and VUV/UV radiation in conjunction with uncharged particles (unshielded plasma conditions) were analyzed in the context of results for the film thickness, morphology, wettability, and surface chemistry obtained for different values of energy/monomer mass.

The film growth rate exhibited strong dependence on the density and energy of ions as well as the density of uncharged particles generated from the plasma and ion-shield surface collisions. The later particles contributed significantly to the film growth process under shielded plasma conditions. Different film growth mechanisms were found under the effect of uncharged particles alone and under the simultaneous effects of ion bombardment, VUV/UV radiation, and uncharged particles from the plasma over a wide range of energy/monomer mass. Microscale film growth comprised the initial deposition of a layer covalently bonded to the polymer substrate, followed by the formation of islands of small asperities and large particles produced from gas phase polymerization. Nanoscale film growth was characterized by the enlargement of surface grains with the increase of plasma intensity. The FC films deposited under shielded plasma conditions and high energy/monomer mass exhibited zone 1 growth structure, while those deposited under unshielded plasma conditions exhibited either zone 3 growth structure (energy/monomer mass less than a threshold value) or grain removal by plasma etching (energy/monomer mass above a critical value).

Contact angle results demonstrated higher film hydrophobicity for shielded plasma conditions and negligible roughness effect on the contact angle measurements. XPS analysis showed that FC films grown under shielded plasma conditions exhibited less crosslinking and higher $CF_2$ concentrations than those grown under unshielded plasma conditions. Chemical analysis revealed that thin FC films with hybrid chemical structures consisting of a crosslinked (strong) interfacial layer and a $CF_2$-rich hydrophobic and compliant surface layer can be grown on polymer surfaces under shielded plasma conditions. The capability to tailor the FC film structure and chemical composition is intriguing and of great importance to biotechnology and various microdevice applications, where control of the surface properties is critical to reliability and performance.

Any one or more features of one or more embodiments may be combined with one or more features of any other embodiment without departing from the scope of the invention.

Any recitation of "a", "an" or "the" is intended to mean "one or more" unless specifically indicated to the contrary.

The above description is illustrative but not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

All references, applications, and patents cited above are herein incorporated by reference in their entirety for all purposes. None is admitted to be prior art.

What is claimed is:

1. An article comprising:
    a polymeric substrate comprising a modified surface, wherein the modified surface is a physically modified surface comprising a crosslinked region;
    a fluorocarbon film on the modified surface of the polymeric substrate,
    wherein the fluorocarbon film is grafted to at least a portion of the polymeric substrate; and
    a biocompatible layer on the fluorocarbon film.

2. The article of claim 1, wherein the article is produced by a process comprising:
    exposing a polymeric substrate to an inductively coupled plasma, thereby creating a modified surface on the polymeric substrate;
    depositing a fluorocarbon film on the modified surface of the polymeric substrate, wherein the fluorocarbon film is grafted to the polymeric substrate; and
    forming a biocompatible layer on the fluorocarbon film.

3. The article of claim 2, wherein at least one of the exposing and the depositing comprises positioning a shield above the polymeric substrate.

4. The article of claim 1 wherein the fluorocarbon film comprises a cross-linked region.

5. The article of claim 4 wherein the fluorocarbon film further comprises an uncrosslinked region, the uncrosslinked region being further from the substrate than the crosslinked region.

6. The article of claim 4, wherein the fluorocarbon film has 46% or less crosslinking.

7. The article of claim 4, wherein the fluorocarbon film has an F/C ratio of 1.60 or more.

8. The article of claim 4, wherein the fluorocarbon film has a connectivity, m, of 2.39 or less.

9. The article of claim 1 wherein the polymeric substrate comprises a low-density or high-density polymeric material.

10. The article of claim 1 wherein the polymeric substrate comprises a low-density polymeric material.

11. The article of claim 1 wherein the biocompatible layer comprises proteins or cells.

12. The article of claim 1 wherein the article comprises a medical device having a tubular structure.

13. The article of claim 1 wherein the article comprises a medical device having a tubular structure, a concave shape, a convex shape, or other shape.

14. The article of claim 1, wherein the modified surface of the polymeric substrate is a chemically modified surface.

15. The article of claim 14, wherein the chemically modified surface comprises polar functional groups.

16. The article of claim 1, wherein the fluorocarbon film has a thickness of 120 nm or less.

17. The article of claim 1, wherein the asperity size and/or asperity height of the fluorocarbon film increases as an energy per monomer mass of the fluorocarbon film increases.

18. The article of claim 1, wherein the fluorocarbon film has a contact angle of 110 degrees or more.

* * * * *